US012578347B2

(12) United States Patent
Kim

(10) Patent No.: US 12,578,347 B2
(45) Date of Patent: Mar. 17, 2026

(54) COMPOSITION FOR PREDICTING CLINICAL STAGE OF ALZHEIMER'S DISEASE AND KIT USING THE SAME

(71) Applicant: Industry-Academic Cooperation Foundation Gyeongsang National University, Jinju-si (KR)

(72) Inventor: Myeong Ok Kim, Jinju-si (KR)

(73) Assignee: Industry-Academic Cooperation Foundation Gyeongsang National University, Jinju-si (KR)

( * ) Notice: Subject to any disclaimer, the term of this patent is extended or adjusted under 35 U.S.C. 154(b) by 1086 days.

(21) Appl. No.: 17/425,599

(22) PCT Filed: Jun. 15, 2020

(86) PCT No.: PCT/KR2020/007701
§ 371 (c)(1),
(2) Date: Jul. 23, 2021

(87) PCT Pub. No.: WO2021/137366
PCT Pub. Date: Jul. 8, 2021

(65) Prior Publication Data
US 2022/0091138 A1      Mar. 24, 2022

(30) Foreign Application Priority Data
Dec. 30, 2019      (KR) ........................ 10-2019-0178233

(51) Int. Cl.
*G01N 33/68* (2006.01)
*C12Q 1/6876* (2018.01)
*C12Q 1/6883* (2018.01)

(52) U.S. Cl.
CPC ....... *G01N 33/6896* (2013.01); *C12Q 1/6876* (2013.01); *C12Q 1/6883* (2013.01); *C12Q 2600/118* (2013.01); *C12Q 2600/158* (2013.01); *G01N 2800/2821* (2013.01)

(58) Field of Classification Search
CPC .. G01N 33/6896; G01N 33/68; C12Q 1/6883; C12Q 1/6876
See application file for complete search history.

(56) References Cited

U.S. PATENT DOCUMENTS

2011/0008780 A1      1/2011   Liew

FOREIGN PATENT DOCUMENTS

| JP | 2009-148247 A | 7/2009 |
| KR | 10-2012-0041821 | 5/2012 |
| KR | 10-2018-0130060 A | 12/2018 |

OTHER PUBLICATIONS

Hino et al., Hum. Mol. Genet., 2017, vol. 16(23):2834-2843.*
Abid et al., Int. J. Mol. Sci., Mar. 11, 2019, vol. 20(5):1219.*
Abid (2019) "Comparative Gene-Expression Analysis of Alzheimer's Disease Progression with Aging in Transgenic Mouse Model," Int. J. Mol. Sci., 20: 1219, 14 pages.
Search Report dated Sep. 24, 2020, corresponding to International Application No. PCT/KR2020/007701 (filed Jun. 15, 2020), a related application, 10 pages.

* cited by examiner

*Primary Examiner* — Xiaozhen Xie
(74) *Attorney, Agent, or Firm* — LEYDIG, VOIT & MAYER, LTD.

(57) ABSTRACT

The composition for predicting Alzheimer's disease prognosis comprising a detection reagent that specifically binds to any one or more genes selected from the group consisting of Nos1 (Nitric oxide synthase 1), Aph1B (Anterior pharynx defective 1 homolog B), Ryr3 (Ryanodine receptor 3), Atf6 (Activating transcriptional factor 6), Ip3r (Inositol trisphosphate receptor), Nep (Neprilysin), Cdk5 (cyclin dependent kinase 5) and Abad (Amyloid beta-binding alcohol dehydrogenase), a kit, and a method for providing information on Alzheimer's disease prognosis of the present invention can rapidly and accurately predict the prognosis of Alzheimer's disease, and can determine the prognosis for a drug by comparing the expression level before and after drug administration, so that an appropriate treatment direction can be determined according to the predicted prognosis. Therefore, they have an effect that can greatly contribute to the reduction of mortality due to Alzheimer's disease.

4 Claims, 10 Drawing Sheets

Specification includes a Sequence Listing.

Endoplasmic Reticulum Stress

SEQUENCE LISTING

```
<160> NUMBER OF SEQ ID NOS: 102

<210> SEQ ID NO 1
<211> LENGTH: 20
<212> TYPE: DNA
<213> ORGANISM: Artificial Sequence
<220> FEATURE:
<223> OTHER INFORMATION: Adam10 primer (F)

<400> SEQUENCE: 1
agccagagtt gtgcgttttt                                              20

<210> SEQ ID NO 2
<211> LENGTH: 20
<212> TYPE: DNA
<213> ORGANISM: Artificial Sequence
<220> FEATURE:
<223> OTHER INFORMATION: Adam10 primer (R)

<400> SEQUENCE: 2
atcgaatcct gccatttcac                                              20

<210> SEQ ID NO 3
<211> LENGTH: 20
<212> TYPE: DNA
<213> ORGANISM: Artificial Sequence
<220> FEATURE:
<223> OTHER INFORMATION: Abad primer (F)

<400> SEQUENCE: 3
cagtgtcatg cccactatgc                                              20

<210> SEQ ID NO 4
<211> LENGTH: 20
<212> TYPE: DNA
<213> ORGANISM: Artificial Sequence
<220> FEATURE:
<223> OTHER INFORMATION: Abad primer (R)

<400> SEQUENCE: 4
gacttccagc gggttatcaa                                              20

<210> SEQ ID NO 5
```

```
<211> LENGTH: 20
<212> TYPE: DNA
<213> ORGANISM: Artificial Sequence
<220> FEATURE:
<223> OTHER INFORMATION: Aph1B primer (F)

<400> SEQUENCE: 5
aatcaccatg aatgcccact                                                  20

<210> SEQ ID NO 6
<211> LENGTH: 20
<212> TYPE: DNA
<213> ORGANISM: Artificial Sequence
<220> FEATURE:
<223> OTHER INFORMATION: Aph1B primer (R)

<400> SEQUENCE: 6
gctgttcagg ctcgcatatt                                                  20

<210> SEQ ID NO 7
<211> LENGTH: 20
<212> TYPE: DNA
<213> ORGANISM: Artificial Sequence
<220> FEATURE:
<223> OTHER INFORMATION: Apo-E primer (F)

<400> SEQUENCE: 7
cagtgccgtc agttcttgtg                                                  20

<210> SEQ ID NO 8
<211> LENGTH: 20
<212> TYPE: DNA
<213> ORGANISM: Artificial Sequence
<220> FEATURE:
<223> OTHER INFORMATION: Apo-E primer (R)

<400> SEQUENCE: 8
gtgctgttgg tcacattgct                                                  20

<210> SEQ ID NO 9
<211> LENGTH: 20
<212> TYPE: DNA
<213> ORGANISM: Artificial Sequence
<220> FEATURE:
<223> OTHER INFORMATION: App primer (F)

<400> SEQUENCE: 9
gttcatgcgc tcgtagatca                                                  20

<210> SEQ ID NO 10
<211> LENGTH: 20
<212> TYPE: DNA
<213> ORGANISM: Artificial Sequence
<220> FEATURE:
<223> OTHER INFORMATION: App primer (R)

<400> SEQUENCE: 10
ggccctcgag aattacatca                                                  20

<210> SEQ ID NO 11
<211> LENGTH: 20
<212> TYPE: DNA
<213> ORGANISM: Artificial Sequence
<220> FEATURE:
<223> OTHER INFORMATION: Atf6 primer (F)

<400> SEQUENCE: 11
```

-continued

_____

```
cccatacttc tggtggcact                                        20

<210> SEQ ID NO 12
<211> LENGTH: 20
<212> TYPE: DNA
<213> ORGANISM: Artificial Sequence
<220> FEATURE:
<223> OTHER INFORMATION: Atf6 primer (R)

<400> SEQUENCE: 12
ggccagactg ttttgctctc                                        20

<210> SEQ ID NO 13
<211> LENGTH: 20
<212> TYPE: DNA
<213> ORGANISM: Artificial Sequence
<220> FEATURE:
<223> OTHER INFORMATION: Serca1 primer (F)

<400> SEQUENCE: 13
gagcccatca gtcaccaagt                                        20

<210> SEQ ID NO 14
<211> LENGTH: 20
<212> TYPE: DNA
<213> ORGANISM: Artificial Sequence
<220> FEATURE:
<223> OTHER INFORMATION: Serca1 primer (R)

<400> SEQUENCE: 14
tggccgatga taacttctcc                                        20

<210> SEQ ID NO 15
<211> LENGTH: 20
<212> TYPE: DNA
<213> ORGANISM: Artificial Sequence
<220> FEATURE:
<223> OTHER INFORMATION: Bace1 primer (F)

<400> SEQUENCE: 15
tacacaccct ttcggaggtc                                        20

<210> SEQ ID NO 16
<211> LENGTH: 20
<212> TYPE: DNA
<213> ORGANISM: Artificial Sequence
<220> FEATURE:
<223> OTHER INFORMATION: Bace1 primer (R)

<400> SEQUENCE: 16
tttgtggaga tggtggacaa                                        20

<210> SEQ ID NO 17
<211> LENGTH: 20
<212> TYPE: DNA
<213> ORGANISM: Artificial Sequence
<220> FEATURE:
<223> OTHER INFORMATION: Bad primer (F)

<400> SEQUENCE: 17
cccaccagga ctggataatg                                        20

<210> SEQ ID NO 18
<211> LENGTH: 20
<212> TYPE: DNA
```

-continued

<213> ORGANISM: Artificial Sequence
<220> FEATURE:
<223> OTHER INFORMATION: Bad primer (R)

<400> SEQUENCE: 18
gggatggagg aggagcttag                                              20

<210> SEQ ID NO 19
<211> LENGTH: 20
<212> TYPE: DNA
<213> ORGANISM: Artificial Sequence
<220> FEATURE:
<223> OTHER INFORMATION: Bid primer (F)

<400> SEQUENCE: 19
gtctggcaat gttgtggatg                                              20

<210> SEQ ID NO 20
<211> LENGTH: 20
<212> TYPE: DNA
<213> ORGANISM: Artificial Sequence
<220> FEATURE:
<223> OTHER INFORMATION: Bid primer (R)

<400> SEQUENCE: 20
tcacagacct gctggtgttc                                              20

<210> SEQ ID NO 21
<211> LENGTH: 20
<212> TYPE: DNA
<213> ORGANISM: Artificial Sequence
<220> FEATURE:
<223> OTHER INFORMATION: Vdcc primer (F)

<400> SEQUENCE: 21
tatgctccca atgacgatga                                              20

<210> SEQ ID NO 22
<211> LENGTH: 20
<212> TYPE: DNA
<213> ORGANISM: Artificial Sequence
<220> FEATURE:
<223> OTHER INFORMATION: Vdcc primer (R)

<400> SEQUENCE: 22
cgttctcatc ctgctcaaca                                              20

<210> SEQ ID NO 23
<211> LENGTH: 20
<212> TYPE: DNA
<213> ORGANISM: Artificial Sequence
<220> FEATURE:
<223> OTHER INFORMATION: Calm1 primer (F)

<400> SEQUENCE: 23
gttctgccgc actgatgtaa                                              20

<210> SEQ ID NO 24
<211> LENGTH: 20
<212> TYPE: DNA
<213> ORGANISM: Artificial Sequence
<220> FEATURE:
<223> OTHER INFORMATION: Calm1 primer (R)

<400> SEQUENCE: 24
actgggtcag aacccaacag                                              20

```
<210> SEQ ID NO 25
<211> LENGTH: 20
<212> TYPE: DNA
<213> ORGANISM: Artificial Sequence
<220> FEATURE:
<223> OTHER INFORMATION: Caln primer (F)

<400> SEQUENCE: 25
aaggcccaca aatacagcac                                                      20

<210> SEQ ID NO 26
<211> LENGTH: 20
<212> TYPE: DNA
<213> ORGANISM: Artificial Sequence
<220> FEATURE:
<223> OTHER INFORMATION: Caln primer (R)

<400> SEQUENCE: 26
cagagggtgc ttcgattctc                                                      20

<210> SEQ ID NO 27
<211> LENGTH: 20
<212> TYPE: DNA
<213> ORGANISM: Artificial Sequence
<220> FEATURE:
<223> OTHER INFORMATION: Casp12 primer (F)

<400> SEQUENCE: 27
tcacgtggac aaagcttcag                                                      20

<210> SEQ ID NO 28
<211> LENGTH: 20
<212> TYPE: DNA
<213> ORGANISM: Artificial Sequence
<220> FEATURE:
<223> OTHER INFORMATION: Casp12 primer (R)

<400> SEQUENCE: 28
ttcccaggaa cagctgagtt                                                      20

<210> SEQ ID NO 29
<211> LENGTH: 20
<212> TYPE: DNA
<213> ORGANISM: Artificial Sequence
<220> FEATURE:
<223> OTHER INFORMATION: Casp3 primer (F)

<400> SEQUENCE: 29
tcccataaat gaccccttca                                                      20

<210> SEQ ID NO 30
<211> LENGTH: 20
<212> TYPE: DNA
<213> ORGANISM: Artificial Sequence
<220> FEATURE:
<223> OTHER INFORMATION: Casp3 primer (R)

<400> SEQUENCE: 30
tgtcatctcg ctctggtacg                                                      20

<210> SEQ ID NO 31
<211> LENGTH: 20
<212> TYPE: DNA
<213> ORGANISM: Artificial Sequence
<220> FEATURE:
```

-continued

<223> OTHER INFORMATION: Casp7 primer (F)

<400> SEQUENCE: 31
cacgggatct gcttcttctc                                         20

<210> SEQ ID NO 32
<211> LENGTH: 20
<212> TYPE: DNA
<213> ORGANISM: Artificial Sequence
<220> FEATURE:
<223> OTHER INFORMATION: Casp7 primer (R)

<400> SEQUENCE: 32
tttgcttact ccacggttcc                                         20

<210> SEQ ID NO 33
<211> LENGTH: 20
<212> TYPE: DNA
<213> ORGANISM: Artificial Sequence
<220> FEATURE:
<223> OTHER INFORMATION: Casp8 primer  (F)

<400> SEQUENCE: 33
gcagaaagtc tgcctcatcc                                         20

<210> SEQ ID NO 34
<211> LENGTH: 20
<212> TYPE: DNA
<213> ORGANISM: Artificial Sequence
<220> FEATURE:
<223> OTHER INFORMATION: Casp8 primer (R)

<400> SEQUENCE: 34
ggcctccatc tatgacctga                                         20

<210> SEQ ID NO 35
<211> LENGTH: 20
<212> TYPE: DNA
<213> ORGANISM: Artificial Sequence
<220> FEATURE:
<223> OTHER INFORMATION: Casp9 primer (F)

<400> SEQUENCE: 35
aagtcccttt cgcagaaaca                                         20

<210> SEQ ID NO 36
<211> LENGTH: 20
<212> TYPE: DNA
<213> ORGANISM: Artificial Sequence
<220> FEATURE:
<223> OTHER INFORMATION: Casp9 primer (R)

<400> SEQUENCE: 36
aagaccatgg ctttgaggtg                                         20

<210> SEQ ID NO 37
<211> LENGTH: 20
<212> TYPE: DNA
<213> ORGANISM: Artificial Sequence
<220> FEATURE:
<223> OTHER INFORMATION: Cdk5 primer (F)

<400> SEQUENCE: 37
acgacgttca ccaaggatgt                                         20

-continued

<210> SEQ ID NO 38
<211> LENGTH: 20
<212> TYPE: DNA
<213> ORGANISM: Artificial Sequence
<220> FEATURE:
<223> OTHER INFORMATION: Cdk5 primer (R)

<400> SEQUENCE: 38
gtccatcgac atgtggtcag                                                        20

<210> SEQ ID NO 39
<211> LENGTH: 20
<212> TYPE: DNA
<213> ORGANISM: Artificial Sequence
<220> FEATURE:
<223> OTHER INFORMATION: P25 primer (F)

<400> SEQUENCE: 39
cccacctcag aggagatgac                                                        20

<210> SEQ ID NO 40
<211> LENGTH: 20
<212> TYPE: DNA
<213> ORGANISM: Artificial Sequence
<220> FEATURE:
<223> OTHER INFORMATION: P25 primer (R)

<400> SEQUENCE: 40
cgtccactag tgagctgctg                                                        20

<210> SEQ ID NO 41
<211> LENGTH: 20
<212> TYPE: DNA
<213> ORGANISM: Artificial Sequence
<220> FEATURE:
<223> OTHER INFORMATION: Cxi primer (F)

<400> SEQUENCE: 41
gggagtgggc ctgaaattag                                                        20

<210> SEQ ID NO 42
<211> LENGTH: 20
<212> TYPE: DNA
<213> ORGANISM: Artificial Sequence
<220> FEATURE:
<223> OTHER INFORMATION: Cxi primer (R)

<400> SEQUENCE: 42
ctctccccag taccctcgac                                                        20

<210> SEQ ID NO 43
<211> LENGTH: 20
<212> TYPE: DNA
<213> ORGANISM: Artificial Sequence
<220> FEATURE:
<223> OTHER INFORMATION: Cxii primer (F)

<400> SEQUENCE: 43
tcaaagttcc caggaagcag                                                        20

<210> SEQ ID NO 44
<211> LENGTH: 20
<212> TYPE: DNA
<213> ORGANISM: Artificial Sequence
<220> FEATURE:
<223> OTHER INFORMATION: Cxii primer (R)

<400> SEQUENCE: 44
cctttgggaa ccacagctaa                                                                20

<210> SEQ ID NO 45
<211> LENGTH: 20
<212> TYPE: DNA
<213> ORGANISM: Artificial Sequence
<220> FEATURE:
<223> OTHER INFORMATION: Cxiii primer (F)

<400> SEQUENCE: 45
tagggccgcg ataataaatg                                                                20

<210> SEQ ID NO 46
<211> LENGTH: 20
<212> TYPE: DNA
<213> ORGANISM: Artificial Sequence
<220> FEATURE:
<223> OTHER INFORMATION: Cxiii primer (R)

<400> SEQUENCE: 46
gttcgcagtc atagccacag                                                                20

<210> SEQ ID NO 47
<211> LENGTH: 20
<212> TYPE: DNA
<213> ORGANISM: Artificial Sequence
<220> FEATURE:
<223> OTHER INFORMATION: Cxiv primer (F)

<400> SEQUENCE: 47
cagccaaaac cagatgacag                                                                20

<210> SEQ ID NO 48
<211> LENGTH: 20
<212> TYPE: DNA
<213> ORGANISM: Artificial Sequence
<220> FEATURE:
<223> OTHER INFORMATION: Cxiv primer (R)

<400> SEQUENCE: 48
gtgtccccac tgatgaggag                                                                20

<210> SEQ ID NO 49
<211> LENGTH: 20
<212> TYPE: DNA
<213> ORGANISM: Artificial Sequence
<220> FEATURE:
<223> OTHER INFORMATION: Cxv primer (F)

<400> SEQUENCE: 49
gataccctgg gtgttgccta                                                                20

<210> SEQ ID NO 50
<211> LENGTH: 20
<212> TYPE: DNA
<213> ORGANISM: Artificial Sequence
<220> FEATURE:
<223> OTHER INFORMATION: Cxv primer (R)

<400> SEQUENCE: 50
gaaactggac caggtggaga                                                                20

<210> SEQ ID NO 51
<211> LENGTH: 20

<212> TYPE: DNA
<213> ORGANISM: Artificial Sequence
<220> FEATURE:
<223> OTHER INFORMATION: Cycs primer (F)

<400> SEQUENCE: 51
tctgcccttt ctcccttctt                                              20

<210> SEQ ID NO 52
<211> LENGTH: 20
<212> TYPE: DNA
<213> ORGANISM: Artificial Sequence
<220> FEATURE:
<223> OTHER INFORMATION: Cycs primer (R)

<400> SEQUENCE: 52
gggaggcaag cataagactg                                              20

<210> SEQ ID NO 53
<211> LENGTH: 20
<212> TYPE: DNA
<213> ORGANISM: Artificial Sequence
<220> FEATURE:
<223> OTHER INFORMATION: Perk primer (F)

<400> SEQUENCE: 53
gttccatctg ggtgctgaat                                              20

<210> SEQ ID NO 54
<211> LENGTH: 20
<212> TYPE: DNA
<213> ORGANISM: Artificial Sequence
<220> FEATURE:
<223> OTHER INFORMATION: Perk primer (R)

<400> SEQUENCE: 54
tggtgactgc tatggaccaa                                              20

<210> SEQ ID NO 55
<211> LENGTH: 20
<212> TYPE: DNA
<213> ORGANISM: Artificial Sequence
<220> FEATURE:
<223> OTHER INFORMATION: Fadd primer (F)

<400> SEQUENCE: 55
aggtcagcca ccagattcag                                              20

<210> SEQ ID NO 56
<211> LENGTH: 20
<212> TYPE: DNA
<213> ORGANISM: Artificial Sequence
<220> FEATURE:
<223> OTHER INFORMATION: Fadd primer (R)

<400> SEQUENCE: 56
acaatgtggg gagagactgg                                              20

<210> SEQ ID NO 57
<211> LENGTH: 20
<212> TYPE: DNA
<213> ORGANISM: Artificial Sequence
<220> FEATURE:
<223> OTHER INFORMATION: Fas primer (F)

<400> SEQUENCE: 57
cctgcatggc agttacacac                                                    20

<210> SEQ ID NO 58
<211> LENGTH: 20
<212> TYPE: DNA
<213> ORGANISM: Artificial Sequence
<220> FEATURE:
<223> OTHER INFORMATION: Fas primer (R)

<400> SEQUENCE: 58
ttgcaagaca tgtcggaaag                                                    20

<210> SEQ ID NO 59
<211> LENGTH: 20
<212> TYPE: DNA
<213> ORGANISM: Artificial Sequence
<220> FEATURE:
<223> OTHER INFORMATION: Appbp1 primer (F)

<400> SEQUENCE: 59
tcttctccgc tgaccagatt                                                    20

<210> SEQ ID NO 60
<211> LENGTH: 20
<212> TYPE: DNA
<213> ORGANISM: Artificial Sequence
<220> FEATURE:
<223> OTHER INFORMATION: Appbp1 primer (R)

<400> SEQUENCE: 60
gcagccaggg aagatactca                                                    20

<210> SEQ ID NO 61
<211> LENGTH: 20
<212> TYPE: DNA
<213> ORGANISM: Artificial Sequence
<220> FEATURE:
<223> OTHER INFORMATION: Gapdh primer (F)

<400> SEQUENCE: 61
acacattggg ggtaggaaca                                                    20

<210> SEQ ID NO 62
<211> LENGTH: 20
<212> TYPE: DNA
<213> ORGANISM: Artificial Sequence
<220> FEATURE:
<223> OTHER INFORMATION: Gapdh primer (R)

<400> SEQUENCE: 62
aagggctcat gaccacagtc                                                    20

<210> SEQ ID NO 63
<211> LENGTH: 20
<212> TYPE: DNA
<213> ORGANISM: Artificial Sequence
<220> FEATURE:
<223> OTHER INFORMATION: Gq primer (F)

<400> SEQUENCE: 63
ggctacacgg tccaagtcat                                                    20

<210> SEQ ID NO 64
<211> LENGTH: 20
<212> TYPE: DNA
<213> ORGANISM: Artificial Sequence -continued

```
<220> FEATURE:
<223> OTHER INFORMATION: Gq primer (R)

<400> SEQUENCE: 64
cacgctcaag atcccataca                                               20

<210> SEQ ID NO 65
<211> LENGTH: 20
<212> TYPE: DNA
<213> ORGANISM: Artificial Sequence
<220> FEATURE:
<223> OTHER INFORMATION: Nmdar primer (F)

<400> SEQUENCE: 65
tttgttcccc aagagtttgc                                               20

<210> SEQ ID NO 66
<211> LENGTH: 20
<212> TYPE: DNA
<213> ORGANISM: Artificial Sequence
<220> FEATURE:
<223> OTHER INFORMATION: Nmdar primer (R)

<400> SEQUENCE: 66
cagcaggact ggtcacagaa                                               20

<210> SEQ ID NO 67
<211> LENGTH: 20
<212> TYPE: DNA
<213> ORGANISM: Artificial Sequence
<220> FEATURE:
<223> OTHER INFORMATION: Gsk3b primer (F)

<400> SEQUENCE: 67
aatttgctcc cttgttggtg                                               20

<210> SEQ ID NO 68
<211> LENGTH: 20
<212> TYPE: DNA
<213> ORGANISM: Artificial Sequence
<220> FEATURE:
<223> OTHER INFORMATION: Gsk3b primer (R)

<400> SEQUENCE: 68
gaggagagcc caatgtttca                                               20

<210> SEQ ID NO 69
<211> LENGTH: 20
<212> TYPE: DNA
<213> ORGANISM: Artificial Sequence
<220> FEATURE:
<223> OTHER INFORMATION: Ide primer (F)

<400> SEQUENCE: 69
gacagccaac atttcctggt                                               20

<210> SEQ ID NO 70
<211> LENGTH: 20
<212> TYPE: DNA
<213> ORGANISM: Artificial Sequence
<220> FEATURE:
<223> OTHER INFORMATION: Ide primer (R)

<400> SEQUENCE: 70
gaggcgttcc aaaaacacat                                               20
```

-continued

```
<210> SEQ ID NO 71
<211> LENGTH: 20
<212> TYPE: DNA
<213> ORGANISM: Artificial Sequence
<220> FEATURE:
<223> OTHER INFORMATION: Il1b primer (F)

<400> SEQUENCE: 71
tccattgagg tggagagctt                                                    20

<210> SEQ ID NO 72
<211> LENGTH: 20
<212> TYPE: DNA
<213> ORGANISM: Artificial Sequence
<220> FEATURE:
<223> OTHER INFORMATION: Il1b primer (R)

<400> SEQUENCE: 72
gaccttccag gatgaggaca                                                    20

<210> SEQ ID NO 73
<211> LENGTH: 20
<212> TYPE: DNA
<213> ORGANISM: Artificial Sequence
<220> FEATURE:
<223> OTHER INFORMATION: Ip3r primer (F)

<400> SEQUENCE: 73
cgatgcagtt ctggttctca                                                    20

<210> SEQ ID NO 74
<211> LENGTH: 20
<212> TYPE: DNA
<213> ORGANISM: Artificial Sequence
<220> FEATURE:
<223> OTHER INFORMATION: Ip3r primer (R)

<400> SEQUENCE: 74
gaatttcctt cgttgccaaa                                                    20

<210> SEQ ID NO 75
<211> LENGTH: 20
<212> TYPE: DNA
<213> ORGANISM: Artificial Sequence
<220> FEATURE:
<223> OTHER INFORMATION: Ire1a primer (F)

<400> SEQUENCE: 75
agaatgttgt ggggcttcag                                                    20

<210> SEQ ID NO 76
<211> LENGTH: 20
<212> TYPE: DNA
<213> ORGANISM: Artificial Sequence
<220> FEATURE:
<223> OTHER INFORMATION: Ire1a primer (R)

<400> SEQUENCE: 76
cccaaatgtg atccgctact                                                    20

<210> SEQ ID NO 77
<211> LENGTH: 20
<212> TYPE: DNA
<213> ORGANISM: Artificial Sequence
<220> FEATURE:
<223> OTHER INFORMATION: Lp1 primer (F)
```

<400> SEQUENCE: 77
gtcaggccag ctgaagtagg                                                    20

<210> SEQ ID NO 78
<211> LENGTH: 20
<212> TYPE: DNA
<213> ORGANISM: Artificial Sequence
<220> FEATURE:
<223> OTHER INFORMATION: Lp1 primer (R)

<400> SEQUENCE: 78
ttttctggga ctgaggatgg                                                    20

<210> SEQ ID NO 79
<211> LENGTH: 20
<212> TYPE: DNA
<213> ORGANISM: Artificial Sequence
<220> FEATURE:
<223> OTHER INFORMATION: Lrp1 primer (F)

<400> SEQUENCE: 79
acaggggttg gtcacttcag                                                    20

<210> SEQ ID NO 80
<211> LENGTH: 20
<212> TYPE: DNA
<213> ORGANISM: Artificial Sequence
<220> FEATURE:
<223> OTHER INFORMATION: Lrp1 primer (R)

<400> SEQUENCE: 80
gacagcaaac gaggcctaag                                                    20

<210> SEQ ID NO 81
<211> LENGTH: 20
<212> TYPE: DNA
<213> ORGANISM: Artificial Sequence
<220> FEATURE:
<223> OTHER INFORMATION: Erk primer (F)

<400> SEQUENCE: 81
agcagatgtg gtcattgctg                                                    20

<210> SEQ ID NO 82
<211> LENGTH: 20
<212> TYPE: DNA
<213> ORGANISM: Artificial Sequence
<220> FEATURE:
<223> OTHER INFORMATION: Erk primer (R)

<400> SEQUENCE: 82
tccttttgag caccagacct                                                    20

<210> SEQ ID NO 83
<211> LENGTH: 20
<212> TYPE: DNA
<213> ORGANISM: Artificial Sequence
<220> FEATURE:
<223> OTHER INFORMATION: Mapt primer (F)

<400> SEQUENCE: 83
gtggagatgt gtccccagac                                                    20

<210> SEQ ID NO 84

-continued

```
<211> LENGTH: 20
<212> TYPE: DNA
<213> ORGANISM: Artificial Sequence
<220> FEATURE:
<223> OTHER INFORMATION: Mapt primer  (R)

<400> SEQUENCE: 84
gtggccaggt ggaagtaaaa                                            20

<210> SEQ ID NO 85
<211> LENGTH: 20
<212> TYPE: DNA
<213> ORGANISM: Artificial Sequence
<220> FEATURE:
<223> OTHER INFORMATION: Ncstn primer (F)

<400> SEQUENCE: 85
gctgctgaag ttggttcctc                                            20

<210> SEQ ID NO 86
<211> LENGTH: 20
<212> TYPE: DNA
<213> ORGANISM: Artificial Sequence
<220> FEATURE:
<223> OTHER INFORMATION: Ncstn primer (R)

<400> SEQUENCE: 86
ctgaccactc tggctccttc                                            20

<210> SEQ ID NO 87
<211> LENGTH: 20
<212> TYPE: DNA
<213> ORGANISM: Artificial Sequence
<220> FEATURE:
<223> OTHER INFORMATION: Nep primer (F)

<400> SEQUENCE: 87
cgaggctggt caaaatgaat                                            20

<210> SEQ ID NO 88
<211> LENGTH: 20
<212> TYPE: DNA
<213> ORGANISM: Artificial Sequence
<220> FEATURE:
<223> OTHER INFORMATION: Nep primer (R)

<400> SEQUENCE: 88
aggcggacaa cctctactca                                            20

<210> SEQ ID NO 89
<211> LENGTH: 20
<212> TYPE: DNA
<213> ORGANISM: Artificial Sequence
<220> FEATURE:
<223> OTHER INFORMATION: Nos1 primer (F)

<400> SEQUENCE: 89
atagtgatgg ccgacctgag                                            20

<210> SEQ ID NO 90
<211> LENGTH: 20
<212> TYPE: DNA
<213> ORGANISM: Artificial Sequence
<220> FEATURE:
<223> OTHER INFORMATION: Nos1 primer(R)

<400> SEQUENCE: 90
```

-continued agcacctacc agctcaagga                                          20

<210> SEQ ID NO 91
<211> LENGTH: 20
<212> TYPE: DNA
<213> ORGANISM: Artificial Sequence
<220> FEATURE:
<223> OTHER INFORMATION: Plcb1 primer (F)

<400> SEQUENCE: 91
ccctttcatg gcttcctgta                                          20

<210> SEQ ID NO 92
<211> LENGTH: 20
<212> TYPE: DNA
<213> ORGANISM: Artificial Sequence
<220> FEATURE:
<223> OTHER INFORMATION: Plcb1 primer (R)

<400> SEQUENCE: 92
catccaggag gtggttcagt                                          20

<210> SEQ ID NO 93
<211> LENGTH: 20
<212> TYPE: DNA
<213> ORGANISM: Artificial Sequence
<220> FEATURE:
<223> OTHER INFORMATION: Psen1 primer (F)

<400> SEQUENCE: 93
tcagccatat tcaccaacca                                          20

<210> SEQ ID NO 94
<211> LENGTH: 20
<212> TYPE: DNA
<213> ORGANISM: Artificial Sequence
<220> FEATURE:
<223> OTHER INFORMATION: Psen1 primer (R)

<400> SEQUENCE: 94
cctcatggcc ctggtattta                                          20

<210> SEQ ID NO 95
<211> LENGTH: 20
<212> TYPE: DNA
<213> ORGANISM: Artificial Sequence
<220> FEATURE:
<223> OTHER INFORMATION: Pen-2 primer (F)

<400> SEQUENCE: 95
gcgagaatga tcacccagaa                                          20

<210> SEQ ID NO 96
<211> LENGTH: 20
<212> TYPE: DNA
<213> ORGANISM: Artificial Sequence
<220> FEATURE:
<223> OTHER INFORMATION: Ryr3 primer (F)

<400> SEQUENCE: 96
cgggtatcca atgaggagaa                                          20

<210> SEQ ID NO 97
<211> LENGTH: 20
<212> TYPE: DNA

-continued

```
<213> ORGANISM: Artificial Sequence
<220> FEATURE:
<223> OTHER INFORMATION: Ryr3 primer (F)

<400> SEQUENCE: 97
atgtcctcca ccttgtctgg                                                  20

<210> SEQ ID NO 98
<211> LENGTH: 20
<212> TYPE: DNA
<213> ORGANISM: Artificial Sequence
<220> FEATURE:
<223> OTHER INFORMATION: Ryr3 primer (R)

<400> SEQUENCE: 98
gtgcagcctc tactcccttg                                                  20

<210> SEQ ID NO 99
<211> LENGTH: 20
<212> TYPE: DNA
<213> ORGANISM: Artificial Sequence
<220> FEATURE:
<223> OTHER INFORMATION: Snca primer (F)

<400> SEQUENCE: 99
caggcatgtc ttccaggatt                                                  20

<210> SEQ ID NO 100
<211> LENGTH: 20
<212> TYPE: DNA
<213> ORGANISM: Artificial Sequence
<220> FEATURE:
<223> OTHER INFORMATION: Snca primer (R)

<400> SEQUENCE: 100
ggagtgacaa cagtggctga                                                  20

<210> SEQ ID NO 101
<211> LENGTH: 20
<212> TYPE: DNA
<213> ORGANISM: Artificial Sequence
<220> FEATURE:
<223> OTHER INFORMATION: Tnf primer (F)

<400> SEQUENCE: 101
cggactccgc aaagtctaag                                                  20

<210> SEQ ID NO 102
<211> LENGTH: 20
<212> TYPE: DNA
<213> ORGANISM: Artificial Sequence
<220> FEATURE:
<223> OTHER INFORMATION: Tnf primer (R)

<400> SEQUENCE: 102
cgtcagccga tttgctatct                                                  20
```

COMPOSITION FOR PREDICTING CLINICAL STAGE OF ALZHEIMER'S DISEASE AND KIT USING THE SAME

CROSS-REFERENCE TO RELATED APPLICATIONS

This application is a U.S. National Stage Application filed under 35 U.S.C. § 371 of International Application No. PCT/KR2020/007701, filed Jun. 15, 2020, which claims the benefit of Korean Application No. KR 10-2019-0178233, filed Dec. 30, 2019. Both of these applications are hereby incorporated by reference in their entireties.

BACKGROUND OF THE INVENTION

1. Field of the Invention

The present invention relates to a composition for predicting clinical stage of Alzheimer's disease comprising an agent for measuring the level of mRNA of a gene combination whose expression is characteristically increased or decreased in Alzheimer's disease or a protein expressed therefrom, and a kit for predicting clinical stage of Alzheimer's disease comprising the same.

2. Description of the Related Art

Alzheimer's disease (AD) is a typical neurodegenerative disease associated with aging. Alzheimer's disease gradually progresses by affecting different areas of the brain starting from the frontal and temporal lobes and then gradually spreading to other parts of the brain. A major pathological feature of Alzheimer's disease is the formation of neurofibrillary tangles (NFTs) in neurons by the amyloid plaques due to accumulation of amyloid beta protein and the tau protein involved in microtubules. The formation of amyloid plaques and neurofibrillary tangles (NFTs) leads to neurodegeneration, synaptic dysfunction and dementia.

Amyloid plaques are produced by amyloid precursor protein (APP). Amyloid precursor protein is a transmembrane protein that penetrates the cell membrane of neurons and is very important for neuron growth, survival and repair after damage. When Alzheimer's disease develops, amyloid precursor protein (APP) is digested and cleaved by γ-secretase and β-secretase to produce amyloid beta composed of 39~43 amino acids. Amyloid beta is produced. This amyloid beta forms amyloid plaques, a densely accumulated mass, on the outside of neurons.

In addition, aberrant aggregation of tau protein is observed in patients with Alzheimer's disease. Tau protein is a protein related to microtubules, which are tube-shaped structures that transport cellular materials in neurons. The phosphorylated tau protein binds microtubules and prevents breakdown, thereby stabilizing neurons. When Alzheimer's disease develops, tau protein is hyperphosphorylated and the tau protein is separated from the microtubules, and the structural stability of the microtubules is reduced, resulting in poor signal transduction in neurons. The hyper-phosphorylated tau protein detached from the microtubules aggregates to form neurofibrillary tangles (NFTs).

The formation of amyloid plaques and neurofibrillary tangles (NFTs) is a major cause of Alzheimer's disease. Currently, deposited amyloid plaques and hyperphosphorylated tau protein are used as diagnostic markers to diagnose Alzheimer's disease. Amyloid-PET (positron emission tomography) was developed as a brain imaging method targeting amyloid beta. However, when it is used, amyloid plaques can be observed even in the elderly with normal cognitive function, resulting in about 35% of patients being misdiagnosed. In addition, although tau-PET has been introduced relatively recently, it has not yet been widely used. Until now, only verification through post-mortem autopsy is considered as a means to definitively diagnose Alzheimer's disease.

In the case of Alzheimer's disease, it is important to diagnose the disease at the stage of dementia as well as at the stage of early prodromal symptoms. Age-related diseases such as Alzheimer's disease have characteristics that make it more difficult to clearly diagnose the disease, so a biological diagnostic tool according to the course of the disease is urgently required. Recently, studies have been conducted to diagnose Alzheimer's disease by measuring the expression level of a genetic marker specifically expressed in Alzheimer's disease. However, relatively few studies have been conducted on genetic markers for predicting the prognosis of Alzheimer's disease patients. Even if Alzheimer's disease diagnosed as being at the same clinical stage, the prognosis varies from patient to patient, so it is of utmost importance to accurately predict the prognosis of Alzheimer's disease for effective treatment of Alzheimer's disease. Gene expression analysis is the most appropriate tool to accurately diagnose multifactorial diseases involving multiple genes, such as Alzheimer's disease.

Accordingly, the present inventors have completed the present invention by confirming that the clinical stage of Alzheimer's disease can be predicted by using the genes whose expression is characteristically increased or decreased selected by analyzing the expression of several genes using an Alzheimer's disease animal model.

SUMMARY OF THE INVENTION

It is an object of the present invention to provide a composition for predicting clinical stage of Alzheimer's disease comprising a reagent for measuring the level of mRNA of a combination of Erk/Mapk2 (extracellular signal-related kinase/mitogen-activated protein kinase 1), Ide (insulin degrading enzyme), Il1b (interleukin beta) and Vdcc (voltage-dependent calcium channel) genes or a protein expressed therefrom.

It is another object of the present invention to provide a composition for predicting clinical stage of Alzheimer's disease comprising a reagent for measuring the level of mRNA of a combination of Cdk5 (cyclin-dependent kinase 5) and Serca1 (sarco/endoplasmic reticulum $Ca^{2+}$ ATPase 1) genes or a protein expressed therefrom.

It is another object of the present invention to provide a composition for predicting clinical stage of Alzheimer's disease comprising a reagent for measuring the level of mRNA of Serca1 (sarco/endoplasmic reticulum $Ca^{2+}$ ATPase 1) gene or a protein expressed therefrom.

It is another object of the present invention to provide a kit for predicting clinical stage of Alzheimer's disease comprising the composition.

To achieve the above objects, the present invention provides a composition for predicting clinical stage of Alzheimer's disease comprising a reagent for measuring the level of mRNA of a combination of Erk/Mapk2 (extracellular signal-related kinase/mitogen-activated protein kinase 1), Ide (insulin degrading enzyme), Il1b (interleukin beta) and Vdcc (voltage-dependent calcium channel) genes or a protein expressed therefrom.

The present invention also provides a composition for predicting clinical stage of Alzheimer's disease comprising a reagent for measuring the level of mRNA of a combination of Cdk5 (cyclin-dependent kinase 5) and Serca1 (sarco/endoplasmic reticulum $Ca^{2+}$ ATPase 1) genes or a protein expressed therefrom.

The present invention also provides a composition for predicting clinical stage of Alzheimer's disease comprising a reagent for measuring the level of mRNA of Serca1 (sarco/endoplasmic reticulum $Ca^{2+}$ ATPase 1) gene or a protein expressed therefrom.

In addition, the present invention provides a kit for predicting clinical stage of Alzheimer's disease comprising the composition.

Advantageous Effect

The gene combination whose expression is characteristically increased or decreased in Alzheimer's disease of the present invention is significantly increased or decreased in expression in the Alzheimer's disease mouse model compared to the normal control group. Therefore, the clinical stage of Alzheimer's disease can be accurately diagnosed or predicted by measuring the expression level of the gene combination, and it can be effectively used to diagnose the onset of the disease quickly.

Figure 1A:
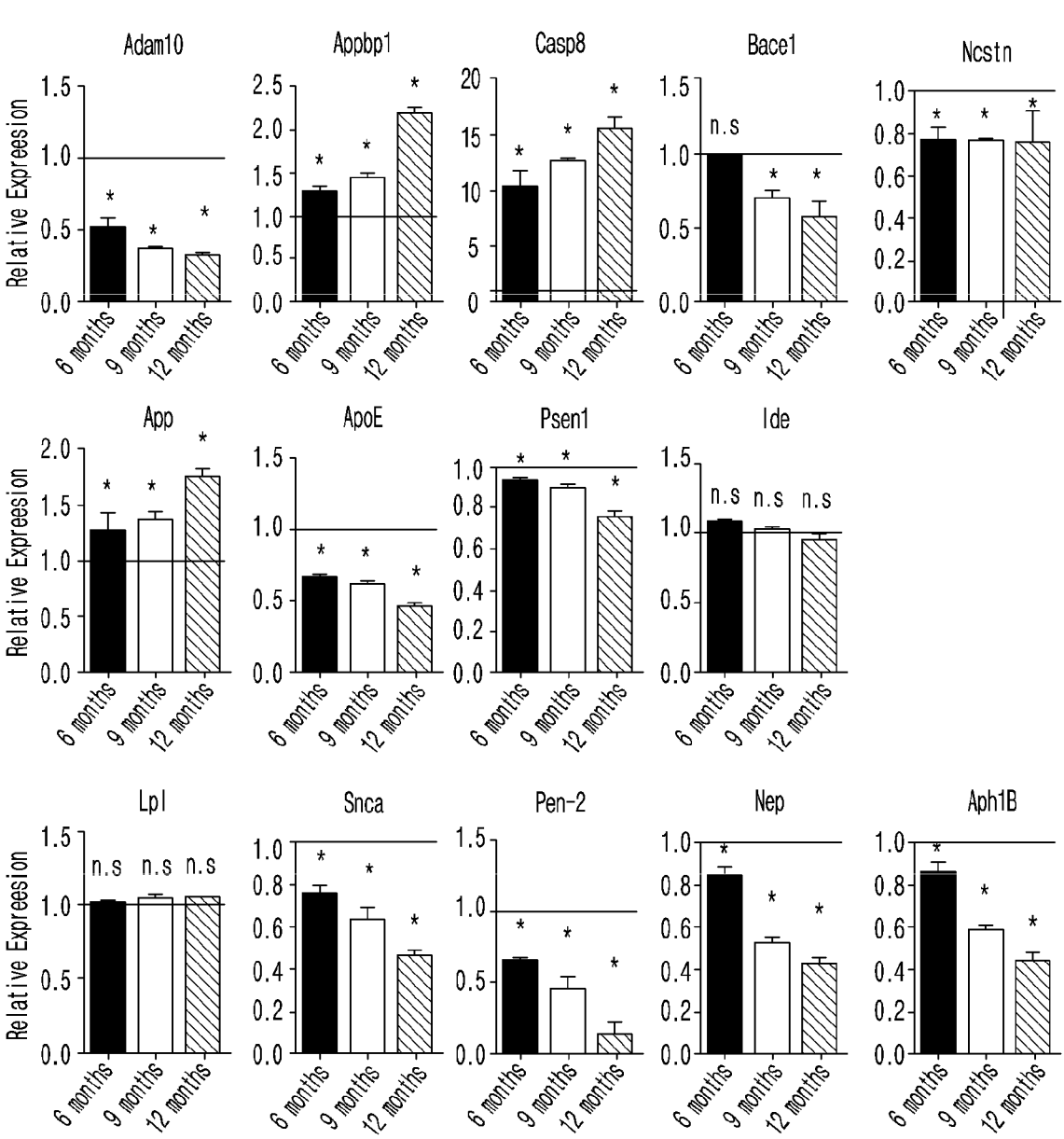
FIG. 1a is a diagram showing the expression level of the normal control mouse gene as 1.0 and the relative expression level of the APP-related gene thereto.

DESCRIPTION OF THE PREFERRED
EMBODIMENTS

Hereinafter, the present invention is described in detail.

The present invention provides a composition for predicting clinical stage of Alzheimer's disease comprising a reagent for measuring the level of mRNA of a combination of Erk/Mapk2 (extracellular signal-related kinase/mitogen-activated protein kinase 1), Ide (insulin degrading enzyme), Il1b (interleukin beta) and Vdcc (voltage-dependent calcium channel) genes or a protein expressed therefrom.

The term 'clinical stage (disease stage)' used in the present invention refers to a period in which the course of a disease is divided according to its characteristics. The clinical stage of Alzheimer's disease is marked by intracellular entanglement of insoluble hyperphosphorylated tau protein and the degree of accumulation of abnormal protein deposits consisting of amyloid beta (Aβ) peptides between neurons. This intracellular entanglement of tau protein and the production of amyloid beta plaques appear in the early stages of Alzheimer's disease, even before symptoms of memory loss and learning loss appear. As Alzheimer's disease progresses, memory loss and learning loss increase when larger areas of the brain are affected by these tangles and plaques. End-stage Alzheimer's disease is characterized by neurodegeneration, neuronal death, and brain shrinkage in a wide range of the brain.

The clinical stages of Alzheimer's disease can be divided into early stage Alzheimer's disease, intermediate stage Alzheimer's disease, and late stage Alzheimer's disease. When amyloid beta plaques are observed only in the isocortex of the brain or in the striatum and entorhinal cortex of the brain, and intracellular entanglement of tau protein is observed in the transentorhinal, it can be diagnosed as early stage Alzheimer's disease. When amyloid beta plaques are observed in the striatum and diencephalon, and intracellular entanglement of tau protein is observed in the limbic system, it can be diagnosed as intermediate stage Alzheimer's disease. When amyloid beta plaques are observed in the various brainstem nerve nuclei or in the cerebellum, and intracellular entanglement of tau protein is widely distributed in the cerebrum cortex (subcortical), it can be diagnosed as late stage Alzheimer's disease.

When the mRNA expression level of the gene is lower than the expression level of mRNA isolated from a normal subject, it can be diagnosed as early stage Alzheimer's disease during the clinical stage.

When the mRNA expression level of the gene is higher than the expression level of mRNA isolated from a normal subject, it can be diagnosed as intermediate or late stage Alzheimer's disease during the clinical stage.

The reagent for measuring the level of mRNA of the gene can be a primer or probe that specifically binds to the gene.

The method for measuring the expression level is preferably selected from the group consisting of reverse transcription polymerase chain reaction (RT-PCR), real-time RT-PCR, competitive RT-PCR, RNase protection assay (RPA), Northern blotting, DNA chip, Western blotting, enzyme-linked immunosorbent assay and radioimmunoassay (RIA), but not always limited thereto.

The reagent for measuring the expression level of the gene is preferably any one selected from the group consisting of primers, probes, anti-sense nucleotides, antibodies, antibody fragments or aptamers that specifically bind to the gene, but not always limited thereto.

The present invention also provides a composition for predicting clinical stage of Alzheimer's disease comprising a reagent for measuring the level of mRNA of a combination of Cdk5 (cyclin-dependent kinase 5) and Serca1 (sarco/endoplasmic reticulum Ca$^{2+}$ ATPase 1) genes or a protein expressed therefrom.

When the mRNA expression levels of Cdk5 (cyclin-dependent kinase 5) and Serca1 (sarco/endoplasmic reticulum Ca$^{2+}$ ATPase 1) genes are higher than the expression level of mRNA isolated from a normal subject, it can be diagnosed as early stage Alzheimer's disease during the clinical stage.

When the mRNA expression level of the gene is lower than the expression level of mRNA isolated from a normal subject, it can be diagnosed as late stage Alzheimer's disease during the clinical stage.

The reagent for measuring the level of mRNA of the gene can be a primer or probe that specifically binds to the gene.

The method for measuring the expression level is preferably selected from the group consisting of reverse transcription polymerase chain reaction (RT-PCR), real-time RT-PCR, competitive RT-PCR, RNase protection assay (RPA), Northern blotting, DNA chip, Western blotting, enzyme-linked immunosorbent assay and radioimmunoassay (RIA), but not always limited thereto.

The reagent for measuring the level of the protein can include an antibody or aptamer specific to the protein.

The reagent for measuring the expression level of the gene is preferably any one selected from the group consisting of primers, probes, anti-sense nucleotides, antibodies, antibody fragments or aptamers that specifically bind to the gene, but not always limited thereto.

The present invention also provides a composition for predicting clinical stage of Alzheimer's disease comprising a reagent for measuring the level of mRNA of Serca1 (sarco/endoplasmic reticulum Ca$^{2+}$ ATPase 1) gene or a protein expressed therefrom.

When the mRNA expression level of the gene is higher than the expression level of mRNA isolated from a normal subject, it can be diagnosed as early stage Alzheimer's disease during the clinical stage.

When the mRNA expression level of the gene is lower than the expression level of mRNA isolated from a normal subject, it can be diagnosed as late stage Alzheimer's disease during the clinical stage.

The method for measuring the expression level is preferably selected from the group consisting of reverse transcription polymerase chain reaction (RT-PCR), real-time RT-PCR, competitive RT-PCR, RNase protection assay (RPA), Northern blotting, DNA chip, Western blotting, enzyme-linked immunosorbent assay and radioimmunoassay (RIA), but not always limited thereto.

The reagent for measuring the level of the protein can include an antibody or aptamer specific to the protein.

The reagent for measuring the expression level of the gene is preferably any one selected from the group consisting of primers, probes, anti-sense nucleotides, antibodies, antibody fragments or aptamers that specifically bind to the gene, but not always limited thereto.

The present invention also provides a kit for predicting clinical stage of Alzheimer's disease comprising the composition.

The kit can be an RT-PCR (reverse transcription polymerase chain reaction) kit, a DNA chip kit, an ELISA (enzyme-linked immunosorbent assay) kit, or a protein chip kit.

The present invention also provides a method for predicting clinical stage of Alzheimer's disease comprising a reagent for measuring the level of mRNA of a combination of Erk/Mapk2 (extracellular signal-related kinase/mitogen-activated protein kinase 1), Ide (insulin degrading enzyme), Il1b (interleukin beta) and Vdcc (voltage-dependent calcium channel) genes or a protein expressed therefrom.

When the mRNA expression level of the gene is lower than the expression level of mRNA isolated from a normal subject, it can be diagnosed as early stage Alzheimer's disease during the clinical stage.

When the mRNA expression level of the gene is higher than the expression level of mRNA isolated from a normal subject, it can be diagnosed as intermediate or late stage Alzheimer's disease during the clinical stage.

The present invention also provides a method for predicting clinical stage of Alzheimer's disease comprising a reagent for measuring the level of mRNA of a combination of Cdk5 (cyclin-dependent kinase 5) and Serca1 (sarco/endoplasmic reticulum Ca$^{2+}$ ATPase 1) genes or a protein expressed therefrom.

When the mRNA expression level of the gene is higher than the expression level of mRNA isolated from a normal subject, it can be diagnosed as early stage Alzheimer's disease during the clinical stage.

When the mRNA expression level of the gene is lower than the expression level of mRNA isolated from a normal subject, it can be diagnosed as late stage Alzheimer's disease during the clinical stage.

In addition, the present invention provides a method for predicting clinical stage of Alzheimer's disease comprising a reagent for measuring the level of mRNA of Serca1 (sarco/endoplasmic reticulum $Ca^{2+}$ ATPase 1) gene or a protein expressed therefrom.

When the mRNA expression level of the gene is higher than the expression level of mRNA isolated from a normal subject, it can be diagnosed as early stage Alzheimer's disease during the clinical stage.

When the mRNA expression level of the gene is lower than the expression level of mRNA isolated from a normal subject, it can be diagnosed as late stage Alzheimer's disease during the clinical stage.

The reagent for measuring the level of mRNA of the gene can be a primer or probe that specifically binds to the gene.

The reagent for measuring the level of the protein can include an antibody or aptamer specific to the protein.

The expression of the combination of Erk/Mapk2 (extracellular signal-related kinase/mitogen-activated protein kinase 1), Ide (insulin degrading enzyme), Il1b (interleukin beta) and Vdcc (voltage-dependent calcium channel) genes of the present invention was significantly decreased in the early stage Alzheimer's disease patients compared to the normal control group, but increased significantly in the intermediate or late stage Alzheimer's disease patients. The expression of the combination of Cdk5 (cyclin-dependent kinase 5) and Serca1 (sarco/endoplasmic reticulum $Ca^{2+}$ ATPase 1) genes was significantly increased in the early stage Alzheimer's disease patients compared to the normal control group, but decreased significantly in the late stage Alzheimer's disease patients. Therefore, the composition and kit of the present invention can be effectively used to predict the clinical stage of Alzheimer's disease.

Hereinafter, the present invention will be described in detail by the following examples and experimental examples.

However, the following examples and experimental examples are only for illustrating the present invention, and the contents of the present invention are not limited thereto.

Example 1: Preparation of Alzheimer's Disease Mouse Model

As the Alzheimer's disease mouse model (AD), B6.Cg-Tg(APPswe, PSEN1dE9)85Dbo/Mmjax double transgenic mice purchased from the Jackson Laboratory (Bar Harbor, ME, USA) were used. These mice express a chimeric mouse-human amyloid precursor protein (APP) bearing the Swedish mutation (Mo/HuAPP695swe), and a mutant human Presenilin 1 protein (PS1-dE9) in neurons of the central nervous system. As the normal control mice (wild type, WT), C57BL/6J mice were purchased from SAMTAKO Korea, and bred under a 12 h light/12 h dark cycle at 25° C. with ad libitum access to food and water. All the experimental procedures were performed with the approval of the Research Ethics Committee of Gyeongsang National University.

Figure 1B:
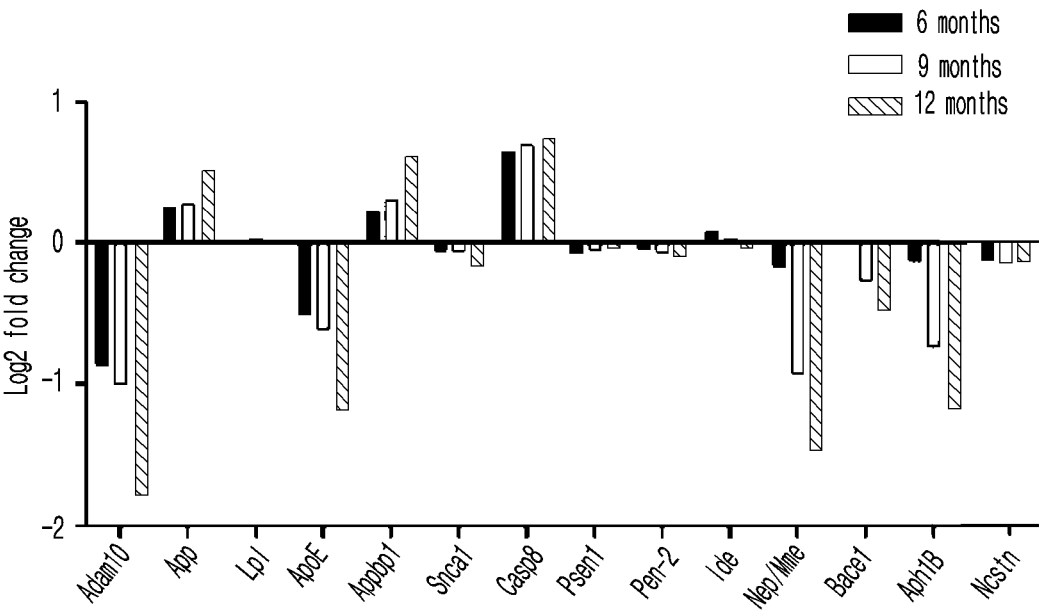
FIG. 1b is a diagram in which the APP-related gene expressed higher than the normal control group was expressed as a positive value, and the gene expressed lower than the normal control group was expressed as a negative value, after obtaining the fold change value based on the gene expression level of the normal control mouse and applying the log 2 value to this value.

Experimental Example 1: Comparison of Gene Expression in Normal Control Mice and Mice with Alzheimer's Disease <1-1> Comparison of APP Protein-Related Gene Expression Since the accumulation of amyloid beta protein, one of the most characteristic features of neurodegeneration, is induced by APP, the expressions of Adam10, App, Lpl, ApoE, Appbp1, Snca, Casp8, Psen1, Pen-2, Ide, Nep, Basel, Ncstn and Aph1b genes in normal control (WT) and mice with Alzheimer's disease (AD) were compared (FIGS. 1a and 1b).

RNA was isolated from the brain hippocampus of 6, 9, and 12 month old Alzheimer's disease model mice and normal control mice using TRIzol reagent (Thermofisher). Before homogenizing the brain tissues, 100 μl of TRIzol reagent was added and incubated at room temperature for 5 minutes. Then, 20 μl of chloroform was added thereto and mixed, followed by further incubation at room temperature for 2 minutes. The mixture was centrifuged at 13000 rpm for 10 minutes at 4° C., the supernatant was transferred to a new tube, to which 250 μg of absolute isopropanol, followed by incubation at room temperature for 10 minutes. Thereafter, the mixture was centrifuged at 13000 rpm for 5 minutes at 4° C. to obtain RNA pellet, which was washed with 250 μg of 75% ethanol. After washing, the RNA pellet was dried at room temperature and suspended in 50 μl of RNase-free water. Of the isolated total RNA, 2 μg of RNA was used for cDNA synthesis. 2 μg of the isolated total RNA was used for cDNA synthesis. RNA was denatured at 65° C. for 10 minutes in a reaction tube, followed by quick cooling on ice. After adding 4 μl of 5×PCR buffer (375 mM KCl and 15 mM $MgCl_2$ in 250 mM Tris-HCl, pH 8.3, Invitrogen, Carlsbad, CA, USA) and 2 μl of 100 mM dithiothreitol (DTT) (Invitrogen) to the reaction tube, and incubating thereof at room temperature for 2 minutes, 200 units of SuperScript™ III Reverse Transcriptase (Invitrogen) was added thereto and reacted at 50° C. for 30 minutes to finally obtain cDNA. A PCR mixture containing dNTPs was used, and in this case, it was generally used at the concentration of 200 nM. The primers were used at the concentration of 0.1 μm.

Distilled water was added to a PCR reaction solution containing 5 μl of the obtained cDNA, 0.1 μm of each gene-specific primer (Table 1, SEQ. ID. NO: 1~NO: 102), and Amplitaq Gold 360 Master Mix (Thermo Fisher Scientific, Waltham, MA, USA) to make a final volume of 25 μl. All PCRs were performed as follows; predenaturation at 94° C. for 5 minutes, denaturation at 94° C. for 45 seconds, annealing at 55° C. for 30 seconds, extension at 72° C. for 45 seconds, 25 cycles from denaturation to extension, and final extension at 72° C. for 7 minutes (Table 2).

20 μl of the amplified PCR product was electrophoresed on a 1.5% TAE gel containing ethidium bromide (EtBr). Then, the APP-related gene expression was quantified through the relative comparison with the expression level of GADPH gene using Gel Doc XR+ Molecular Imager System (Bio-Rad, Hercules, CA, USA) densitometry.

As a result, the expressions of App, Appbp1 and Casp8 were significantly increased in the mice with Alzheimer's disease compared to the normal control group mice, the expressions of Adam10, ApoE, Psen1, Pen-2, Nep, Bace1, Aph1b and Snca were significantly decreased, and the expression of Ide was not different (FIGS. 1a and 1b). Among them, Nep and Aph1b genes whose expressions were most significantly changed were selected.

TABLE 1

| Gene | Reverse primer (5'->3') | SEQ ID NO | Forward primer (5'->3') | SEQ ID NO |
|---|---|---|---|---|
| Adam10 | atcgaatcctgccatttcac | 2 | agccagagttgtgcgttttt | 1 |
| Abad | gacttccagcgggttatcaa | 4 | cagtgtcatgcccactatgc | 3 |
| Aph1B | gctgttcaggctcgcatatt | 6 | aatcaccatgaatgcccact | 5 |
| Apo-E | gtgctgttggtcacattgct | 8 | cagtgccgtcagttcttgtg | 7 |
| App | ggccctcgagaattacatca | 10 | gttcatgcgctcgtagatca | 9 |
| Atf6 | ggccagactgttttgctctc | 12 | cccatacttctggtggcact | 11 |
| Serca1 | tggccgatgataacttctcc | 14 | gagcccatcagtcaccaagt | 13 |
| Bace1 | tttgtggagatggtggacaa | 16 | tacacaccctttcggaggtc | 15 |
| Bad | gggatggaggaggagcttag | 18 | cccaccaggactggataatg | 17 |
| Bic | tcacagacctgctggtgttc | 20 | gtctggcaatgttgtggatg | 19 |
| Vdcc | cgttctcatcctgctcaaca | 22 | tatgctcccaatgacgatga | 21 |
| Calm1 | actgggtcagaacccaacag | 24 | gttctgccgcactgatgtaa | 23 |
| Caln | cagagggtgcttcgattctc | 26 | aaggcccacaaatacagcac | 25 |
| Casp12 | ttcccaggaacagctgagtt | 28 | tcacgtggacaaagcttcag | 27 |
| Casp3 | tgtcatctcgctctggtacg | 30 | tcccataaatgaccccttca | 29 |
| Casp7 | tttgcttactccacggttcc | 32 | cacgggatctgcttcttctc | 31 |
| Casp8 | ggcctccatctatgacctga | 34 | gcagaaagtctgcctcatcc | 33 |
| Casp9 | aagaccatggctttgaggtg | 36 | aagtccctttcgcagaaaca | 35 |
| Cdk5 | gtccatcgacatgtggtcag | 38 | acgacgttcaccaaggatgt | 37 |
| P25 | cgtccactagtgagctgctg | 40 | cccacctcagaggagatgac | 39 |
| Cxi | ctctccccagtaccctcgac | 42 | gggagtgggcctgaaattag | 41 |
| Cxii | cctttgggaaccacagctaa | 44 | tcaaagttcccaggaagcag | 43 |
| Cxiii | gttcgcagtcatagccacag | 46 | tagggccgcgataataaatg | 45 |
| Cxiv | gtgtccccactgatgaggag | 48 | cagccaaaaccagatgacag | 47 |
| Cxv | gaaactggaccaggtggaga | 50 | gatacctgggtgttgccta | 49 |
| Cycs | gggaggcaagcataagactg | 52 | tctgccctttctcccttctt | 51 |
| Perk | tggtgactgctatggaccaa | 54 | gttccatctgggtgctgaat | 53 |
| Fadd | acaatgtggggagagactgg | 56 | aggtcagccaccagattcag | 55 |
| Fas | ttgcaagacatgtcggaaag | 58 | cctgcatggcagttacacac | 57 |
| Appbp1 | gcagccagggaagatactca | 60 | tcttctccgctgaccagatt | 59 |
| Gapdh | aagggctcatgaccacagtc | 62 | acacattgggggtaggaaca | 61 |
| Gq | cacgctcaagatcccataca | 64 | ggctacacggtccaagtcat | 63 |
| Nmdar | cagcaggactggtcacagaa | 66 | tttgttccccaagagtttgc | 65 |
| Gsk3b | gaggagagcccaatgtttca | 68 | aatttgctcccttgttggtg | 67 |
| Ide | gaggcgttccaaaaacacat | 70 | gacagccaacatttcctggt | 69 |
| II1b | gaccttccaggatgaggaca | 72 | tccattgaggtggagagctt | 71 |
| Ip3r | gaatttccttcgttgccaaa | 74 | cgatgcagttctggttctca | 73 |
| Ire1a | cccaaatgtgatccgctact | 76 | agaatgttgtggggcttcag | 75 |
| Lpl | tttctgggactgaggatgg | 78 | gtcaggccagctgaagtagg | 77 |

TABLE 1-continued

| Gene | Reverse primer (5'->3') | SEQ ID NO | Forward primer (5'->3') | SEQ ID NO |
|---|---|---|---|---|
| Lrp1 | gacagcaaacgaggcctaag | 80 | acaggggttggtcacttcag | 79 |
| Erk | tccttttgagcaccagacct | 82 | agcagatgtggtcattgctg | 81 |
| Mapt | gtggccaggtggaagtaaaa | 84 | gtggagatgtgtccccagac | 83 |
| Ncstn | ctgaccactctggctccttc | 86 | gctgctgaagttggttcctc | 85 |
| Nep | aggcggacaacctctactca | 88 | cgaggctggtcaaaatgaat | 87 |
| Nos1 | agcacctaccagctcaagga | 90 | atagtgatggccgacctgag | 89 |
| Plcb1 | catccaggaggtggttcagt | 92 | ccctttcatggcttcctgta | 91 |
| Psen1 | cctcatggccctggtattta | 94 | tcagccatattcaccaacca | 93 |
| Pen-2 | cgggtatccaatgaggagaa | 96 | gcgagaatgatcacccagaa | 95 |
| Ryr3 | gtgcagcctctactcccttg | 98 | atgtcctccaccttgtctgg | 97 |
| Snca | ggagtgacaacagtggctga | 100 | caggcatgtcttccaggatt | 99 |
| Tnf | cgtcagccgatttgctatct | 102 | cggactccgcaaagtctaag | 101 |

TABLE 2

| Temperature (° C.) | Time | Cycle number |
|---|---|---|
| 94 | 5 minutes | 1 |
| 94 | 45 seconds | 25 |
| 55 | 30 seconds | 25 |
| 72 | 45 seconds | 25 |
| 72 | 7 minutes | 1 |

<1-2> Comparison of Tau Protein-Related Gene Expression

Tau protein is a protein involved in microtubule stabilization. The hyperphosphorylation of tau protein in Alzheimer's disease is responsible for microtubule destabilization, thus leading to neurodegeneration and deficits in synaptic transmission and memory. Therefore, the expressions of tau-related genes were compared in the normal control group mice and the mice with Alzheimer's disease.

Figure 2A:
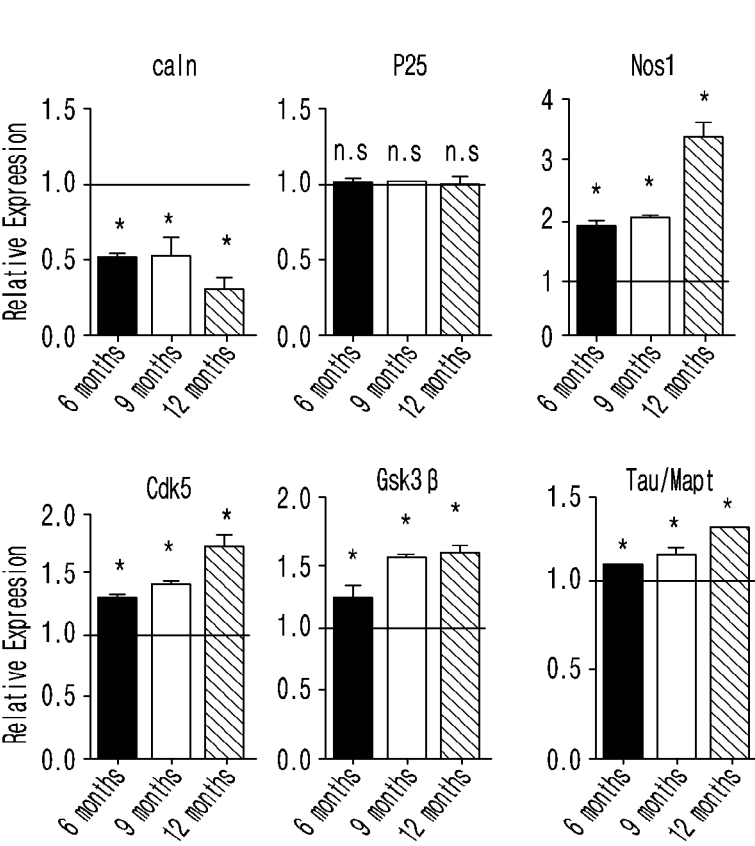
FIG. 2a is a diagram showing the expression level of the normal control mouse gene as 1.0 and the relative expression level of the tau protein-related gene thereto.
Figure 2B:
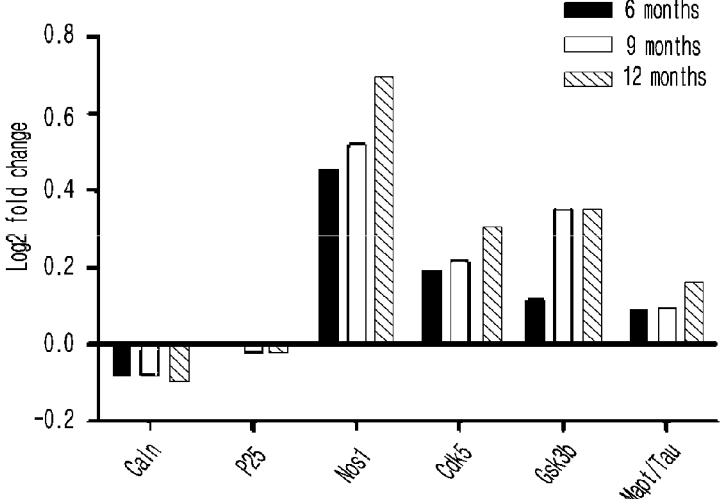
FIG. 2b is a diagram in which the tau protein-related gene expressed higher than the normal control group was expressed as a positive value, and the gene expressed lower than the normal control group was expressed as a negative value, after obtaining the fold change value based on the gene expression level of the normal control mouse and applying the log 2 value to this value.

Particularly, the expressions of the Caln, Nos1, Gsk3b, Mapt/tau, P25 and Cdk5 genes related to the hyperphosphorylation of tau protein were shown in FIGS. 2a and 2b as the relative expression levels to those of the normal control group by performing RT-PCR as described in Experimental Example <1-1>.

As a result, the expressions of Nos1, Gsk3b, Mapk/tau and Cdk5 were significantly increased in the mice with Alzheimer's disease compared to the normal control group mice, the expression of Caln was significantly decreased, and the expression of P25 was not different (FIGS. 2a and 2b). Among them, Nos1 and Cdk5 genes whose expressions were most significantly changed were selected.

<1-3> Comparison of Endoplasmic Reticulum Stress-Related Gene Expression

ER dysfunction due to endoplasmic reticulum stress is known to play an important role in the pathogenesis of Alzheimer's disease. ER stress is associated with mutations in presenilin 1 and presenilin 2 proteins, amyloid beta production, tau protein hyperphosphorylation, and apoptosis. Therefore, the expressions of the genes related to ER stress were compared in the normal control group mice and the mice with Alzheimer's disease.

Figure 3A:
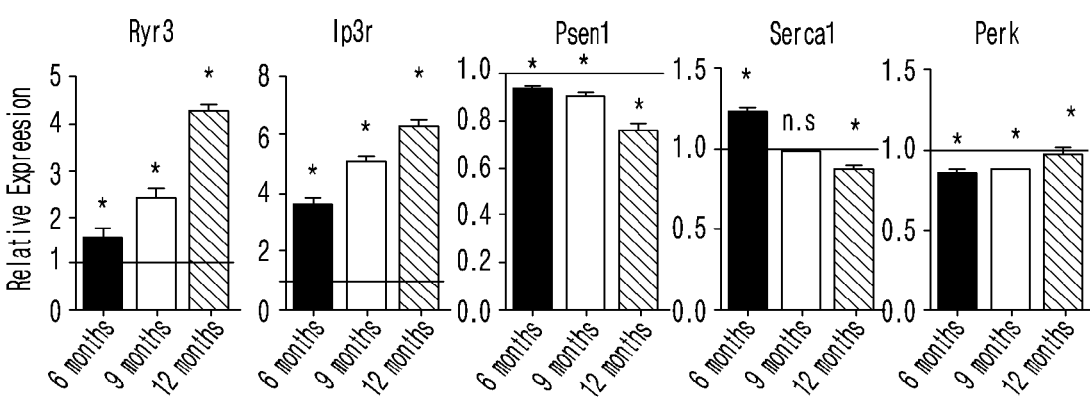
FIG. 3a is a diagram showing the expression level of the normal control mouse gene as 1.0 and the relative expression level of the endoplasmic reticulum stress-related gene thereto.
Figure 3A:
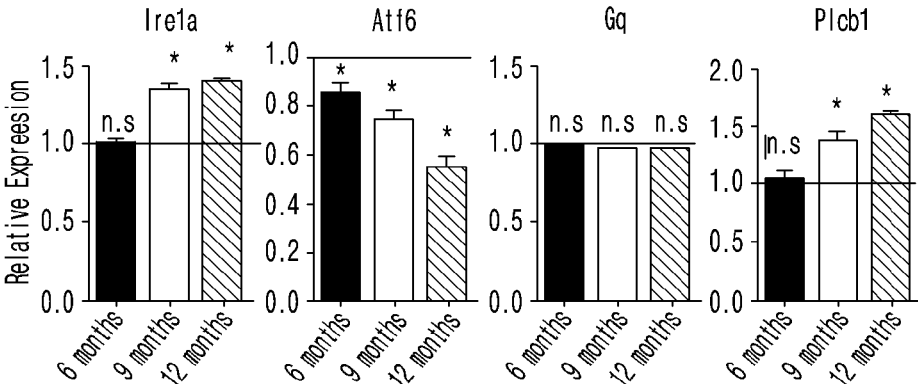
Figure 3B:
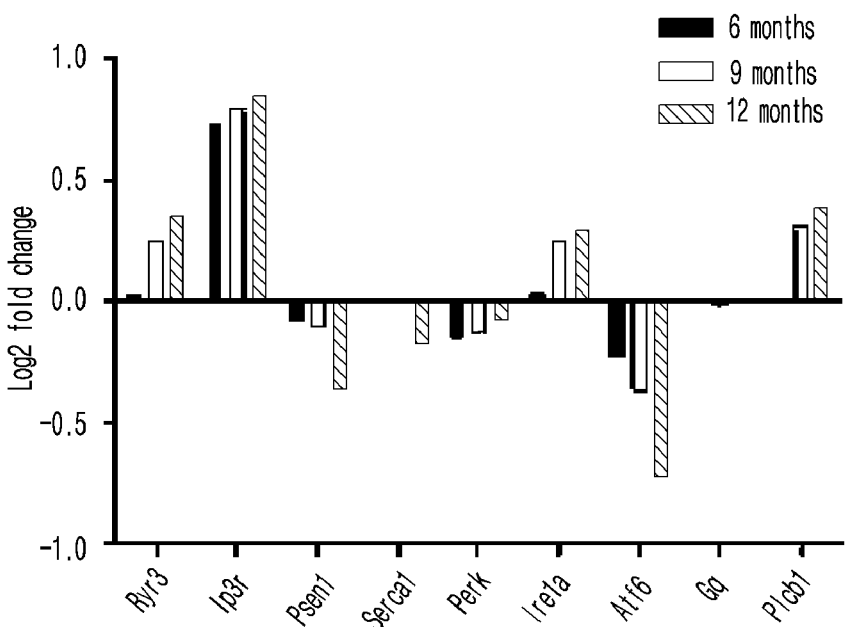
FIG. 3b is a diagram in which the endoplasmic reticulum stress-related gene expressed higher than the normal control group was expressed as a positive value, and the gene expressed lower than the normal control group was expressed as a negative value, after obtaining the fold change value based on the gene expression level of the normal control mouse and applying the log 2 value to this value.

Particularly, the expressions of the Ryr3, Ip3r, Psen1, Serca1, Perk, Ire1a, Atf6, Gq and Plcb1 genes related to ER stress were shown in FIGS. 3a and 3b as the relative expression levels to those of the normal control group by performing RT-PCR as described in Experimental Example <1-1>.

As a result, the expressions of Ryr3, Ip3R, Ire1a and Plcb1 were significantly increased in the mice with Alzheimer's disease compared to the normal control group mice, the expressions of Perk, Psen1, Serca1 and Atf6 were significantly decreased, and the expression of Gq was not different (FIGS. 3a and 3b). Among them, Atf6, Ip3R and Ryr3 genes whose expressions were most significantly changed were selected.

<1-4> Comparison of Calcium Signaling Disruption-Related Gene Expression

Calcium signaling disruption, induced by amyloid beta protein, is associated with memory dysfunction because a persistent increase in calcium level enhances long-term potentiation and synaptic transmission. Therefore, the expressions of the genes related to calcium signaling were compared in the normal control group mice and the mice with Alzheimer's disease.

Figure 4A:
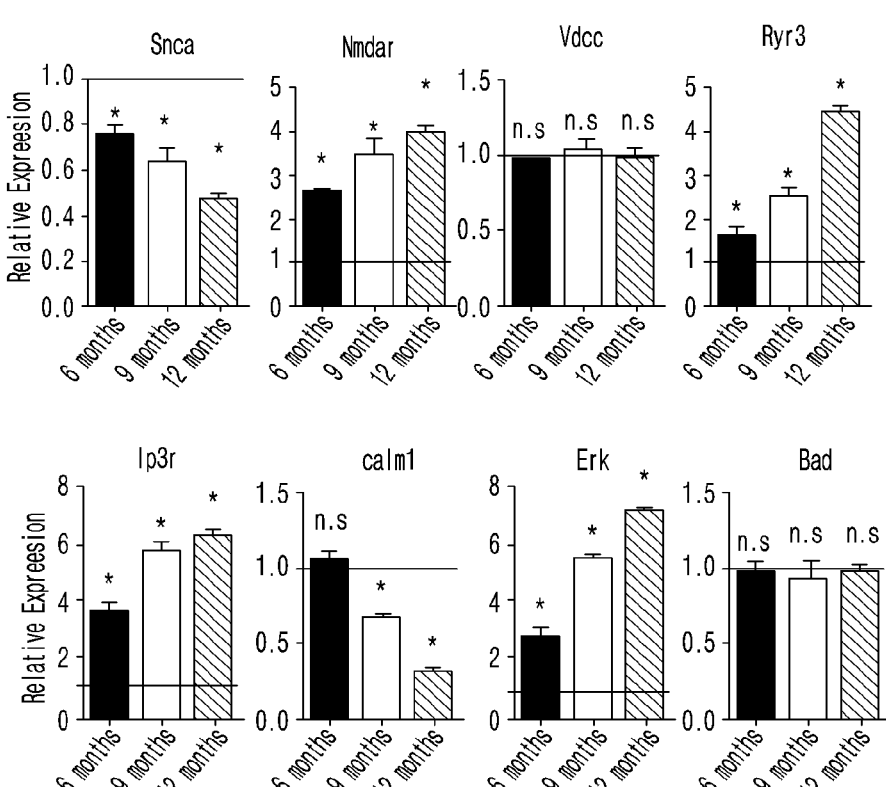
FIG. 4a is a diagram showing the expression level of the normal control mouse gene as 1.0 and the relative expression level of the calcium signaling disruption-related gene thereto.
Figure 4B:
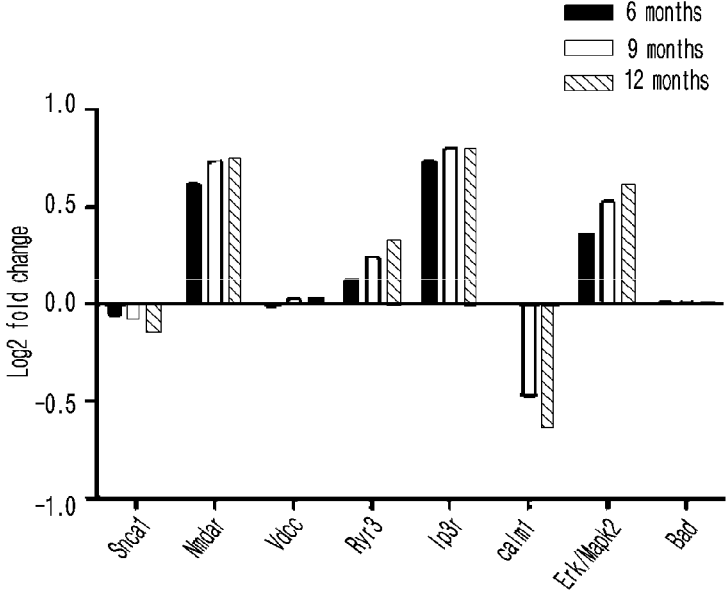
FIG. 4b is a diagram in which the calcium signaling disruption-related gene expressed higher than the normal control group was expressed as a positive value, and the gene expressed lower than the normal control group was expressed as a negative value, after obtaining the fold change value based on the gene expression level of the normal control mouse and applying the log 2 value to this value.

Particularly, the expressions of the Nmdar, Vdcc, Ryr3, Ip3r, Calm1, Erk/Mapk2 and Bad genes related to calcium signaling were shown in FIGS. 4a and 4b as the relative expression levels to those of the normal control group by performing RT-PCR as described in Experimental Example <1-1>.

As a result, the expressions of Nmdar, Ryr3, Ip3r and Erk/Mapk2 were significantly increased in the mice with Alzheimer's disease compared to the normal control group mice, the expressions of Calm1 and Snca were significantly decreased, and the expressions of Vdcc and Bad were not different (FIGS. 4a and 4b).

<1-5> Comparison of Mitochondrial Dysfunction-Related Gene Expression

In the brains of Alzheimer's disease patients, mitochondrial function is disrupted because of amyloid beta protein accumulation. Mitochondrial dysfunction leads to reactive oxygen species (ROS) and inflammation, which cause neurodegeneration and cell death. Therefore, the expressions of the genes related to mitochondrial dysfunction were compared in the normal control group mice and the mice with Alzheimer's disease.

Figure 5A:
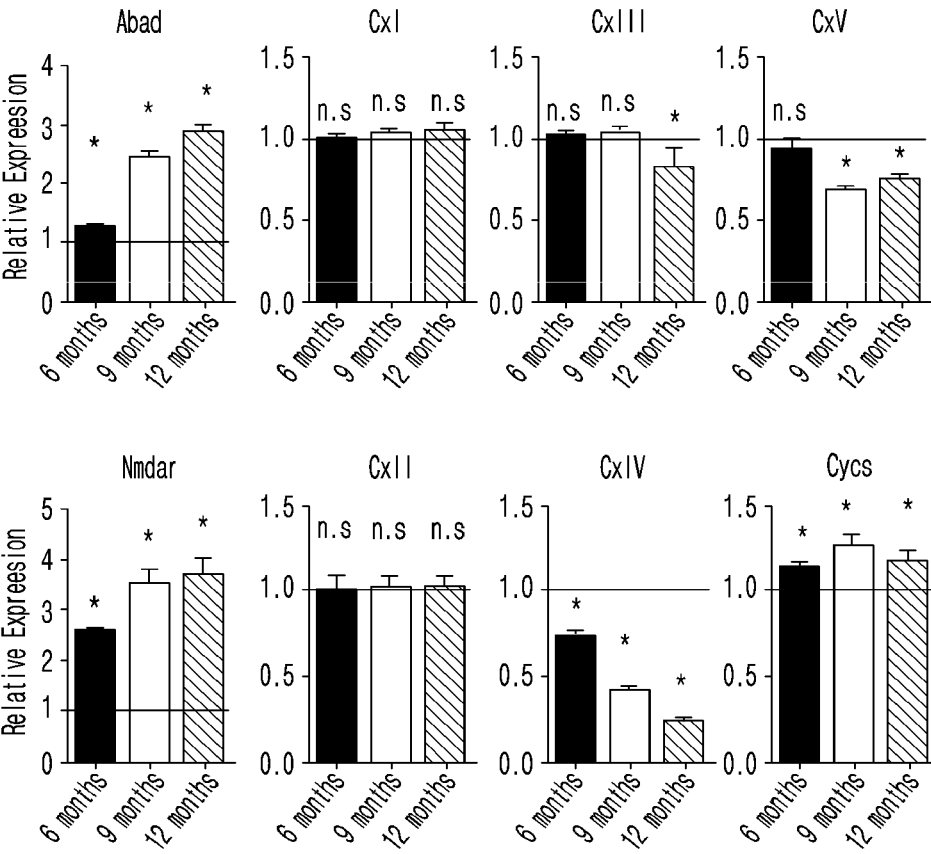
FIG. 5a is a diagram showing the expression level of the normal control mouse gene as 1.0 and the relative expression level of the mitochondrial dysfunction-related gene thereto.
Figure 5B:
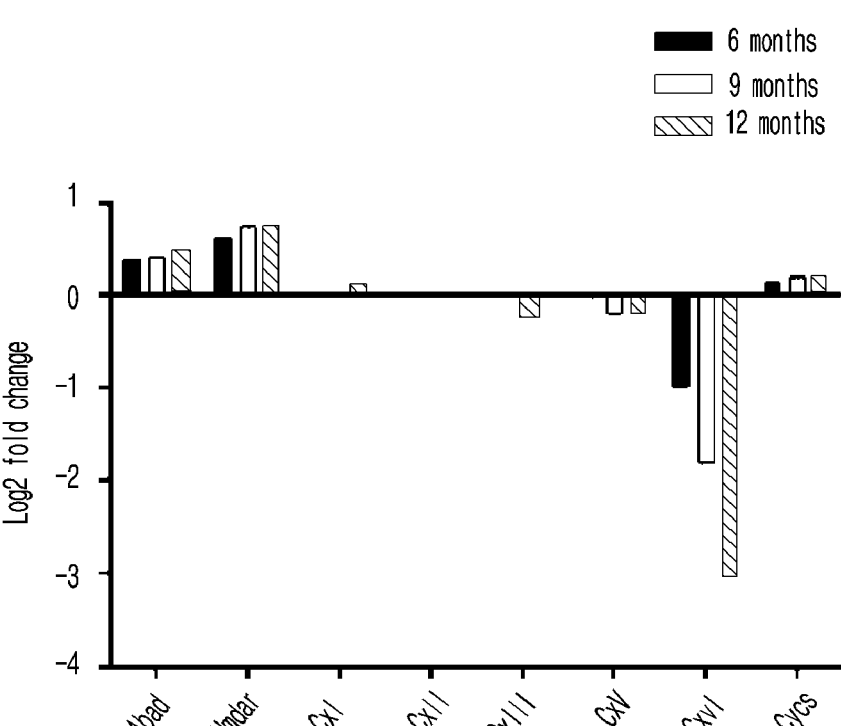
FIG. 5b is a diagram in which the mitochondrial dysfunction-related gene expressed higher than the normal control group was expressed as a positive value, and the gene expressed lower than the normal control group was expressed as a negative value, after obtaining the fold change value based on the gene expression level of the normal control mouse and applying the log 2 value to this value.

Particularly, the expressions of the Abad, Nmdar, Cx 1-5 and Cycs genes related to mitochondrial dysfunction were shown in FIGS. 5a and 5b as the relative expression levels to those of the normal control group by performing RT-PCR as described in Experimental Example <1-1>.

As a result, the expressions of Abad, Nmdar and Cycs were significantly increased in the mice with Alzheimer's disease compared to the normal control group mice, the expressions of Cx3, Cx4 and Cx5 were significantly decreased, and the expressions of Cx1 and Cx2 were not different (FIGS. 5a and 5b). Among them, Abad gene whose expression was most significantly changed was selected.

<1-6> Comparison of Inflammation and Apoptosis-Related Gene Expression

Inflammation and apoptosis are the final pathological events in the onset of Alzheimer's disease. Therefore, the expressions of the genes related to inflammation and apoptosis were compared in the normal control group mice and the mice with Alzheimer's disease.

Figure 6A:
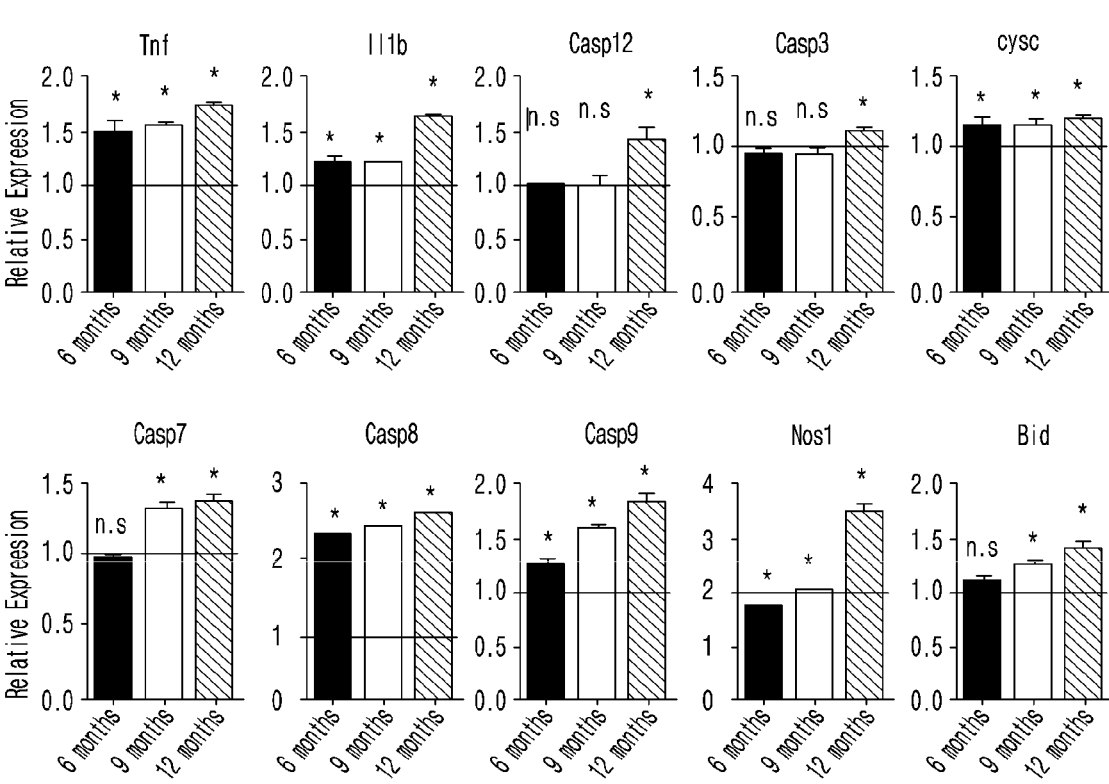
FIG. 6a is a diagram showing the expression level of the normal control mouse gene as 1.0 and the relative expression level of the inflammation and apoptosis-related gene thereto.
Figure 6B:
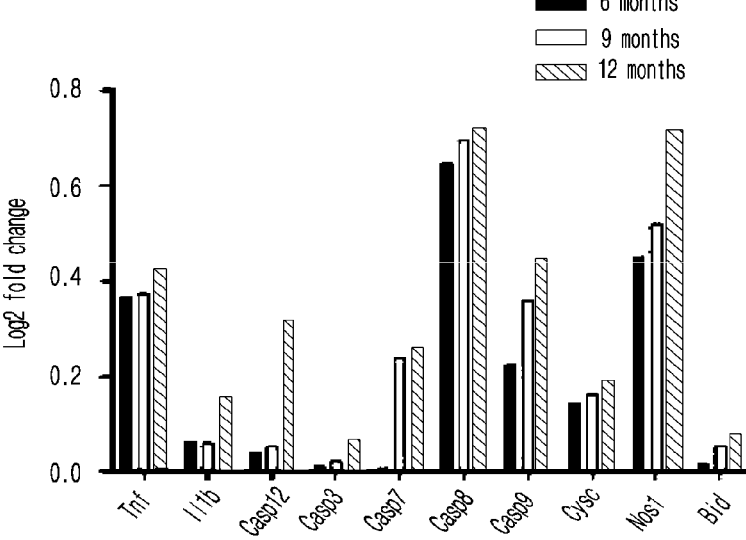
FIG. 6b is a diagram in which the inflammation and apoptosis-related gene expressed higher than the normal control group was expressed as a positive value, and the gene expressed lower than the normal control group was expressed as a negative value, after obtaining the fold change value based on the gene expression level of the normal control mouse and applying the log 2 value to this value.

Particularly, the expressions of the Tnf, Il1b, Casp12, Casp3, Casp7, Casp9, Cycs, Nos1 and Bid genes related to inflammation were shown in FIGS. 6a and 6b as the relative expression levels to those of the normal control group by performing the method described in Experimental Example 1.

As a result, the expressions of Tnf, Il1b, Casp12, Casp3, Casp7, Casp9, Cycs, Nos1 and Bid were all significantly increased in the mice with Alzheimer's disease compared to the normal control group mice (FIGS. 6a and 6b). Among them, Nos1 gene whose expression was most significantly changed was selected.

Experimental Example 2: Comparison of Gene Expression in Mice with Alzheimer's Disease by Age (6, 9, and 12 Months)

<2-1> Comparison of APP Protein-Related Gene Expression

Since the accumulation of amyloid beta protein, one of the most characteristic features of neurodegeneration, is induced by APP, the expressions of APP-related genes by age in mice with Alzheimer's disease were compared.

Figure 1C:
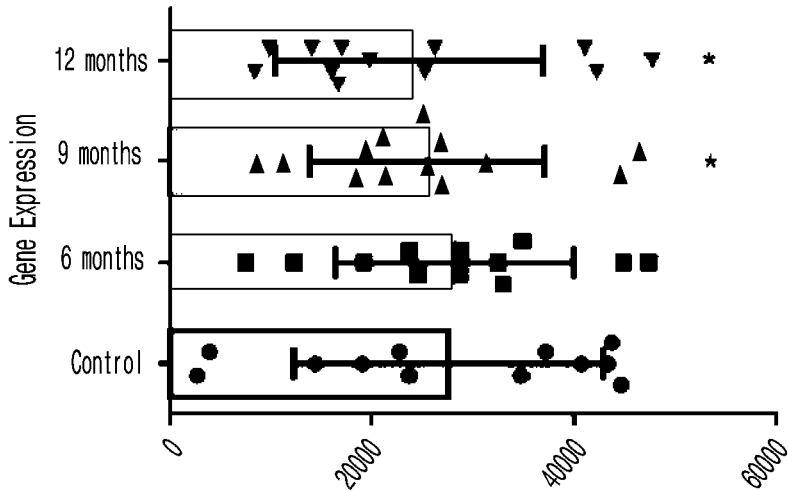
FIG. 1c is a scattered dot plot showing the expression level of the APP-related gene by month after the onset of Alzheimer's disease.

Particularly, the expressions of the Adam10, App, Lpl, ApoE, Appbp1, Snca, Casp8, Psen1, Pen-2, Ide, Nep, Bace1, Ncstn and Aph1b genes related to APP protein by age were shown in FIGS. 1a and 1c by performing RT-PCR as described in Experimental Example <1-1>.

As a result, the expressions of Adam10, Bace1, ApoE, Psen1, Snca, Pen-2, Nep and Aph1B were gradually decreased as the disease progressed, and the expressions of Appbp1, Casp8 and App were gradually increased. The expressions of Lpl and Ide did not change even as the disease progressed (FIG. 1a). In addition, it was confirmed that the expressions of the APP protein-related genes were decreased as Alzheimer's disease progressed (FIG. 1c). Therefore, it was confirmed that the prognosis of Alzheimer's disease can be predicted using the Nep and Aph1b genes whose expressions were most significantly changed.

<2-2> Comparison of Tau Protein-Related Gene Expression

Tau protein is a protein involved in microtubule stabilization. The hyperphosphorylation of tau protein in Alzheimer's disease is responsible for microtubule destabilization, thus leading to neurodegeneration and deficits in synaptic transmission and memory. Therefore, the expressions of tau-related genes by age in mice with Alzheimer's disease were compared.

Figure 2C:
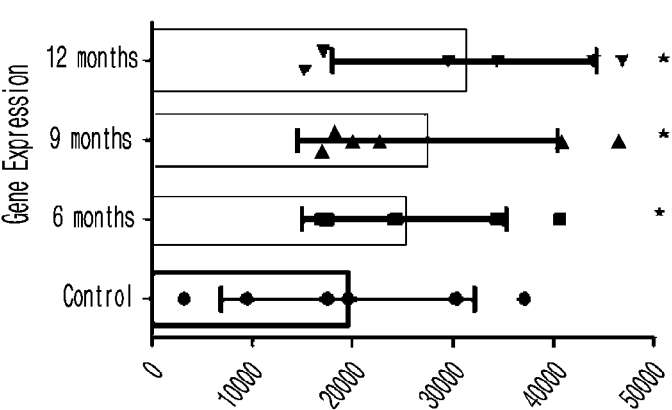
FIG. 2c is a scattered dot plot showing the expression level of the tau protein-related gene by month after the onset of Alzheimer's disease.

Particularly, the expressions of the Caln, Nos1, Gsk3b, Mapt/tau, P25 and Cdk5 genes related to the hyperphosphorylation of tau protein by age were shown in FIGS. 2a and 2c by performing RT-PCR as described in Experimental Example <1-1>.

As a result, the expressions of Nos1, Gsk3b, Mapk/tau and Cdk5 were gradually increased as the disease progressed, and the expression of Caln was gradually decreased. The expression of P25 did not change even as the disease progressed (FIG. 2a). In addition, it was confirmed that the expressions of the APP protein-related genes were increased as Alzheimer's disease progressed (FIG. 2c). Therefore, it was confirmed that the prognosis of Alzheimer's disease can be predicted using the Nos1 and Cdk5 genes whose expressions were most significantly changed.

<2-3> Comparison of Endoplasmic Reticulum Stress-Related Gene Expression

ER dysfunction due to endoplasmic reticulum stress is known to play an important role in the pathogenesis of Alzheimer's disease. ER stress is associated with mutations in presenilin 1 and presenilin 2 proteins, amyloid beta production, tau protein hyperphosphorylation, and apoptosis. Therefore, the expressions of the genes related to ER stress by age in mice with Alzheimer's disease were compared.

Figure 3C:
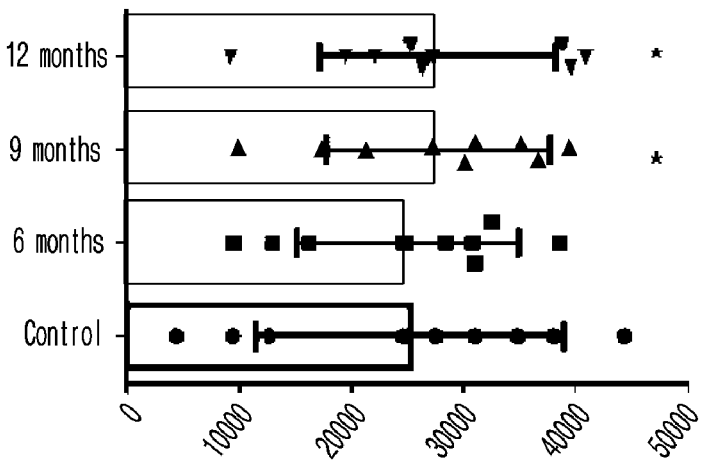
FIG. 3c is a scattered dot plot showing the expression level of the endoplasmic reticulum stress-related gene by month after the onset of Alzheimer's disease.

Particularly, the expressions of the Ryr3, Ip3r, Psen1, Serca1, Perk, Ire1a, Atf6, Gq and Plcb1 genes related to ER stress by age were shown in FIGS. 3a and 3c by performing RT-PCR as described in Experimental Example <1-1>.

As a result, the expressions of Ryr3, Ip3R, Ire1a, Plcb1, Perk and Plcb1 were gradually increased as the disease progressed, and the expressions of Psen1, Serca1 and Atf6 were gradually decreased. The expression of Gp did not change even as the disease progressed (FIG. 3a). In addition, it was confirmed that the expressions of the genes related to ER stress were increased as Alzheimer's disease progressed (FIG. 3c). Therefore, it was confirmed that the prognosis of Alzheimer's disease can be predicted using the Ryr3, Ip3R and Atf6 genes whose expressions were most significantly changed.

<2-4> Comparison of Calcium Signaling Disruption-Related Gene Expression

Calcium signaling disruption, induced by amyloid beta protein, is associated with memory dysfunction because a persistent increase in calcium level enhances long-term potentiation and synaptic transmission. Therefore, the expressions of the genes related to calcium signaling by age in mice with Alzheimer's disease were compared.

Figure 4C:
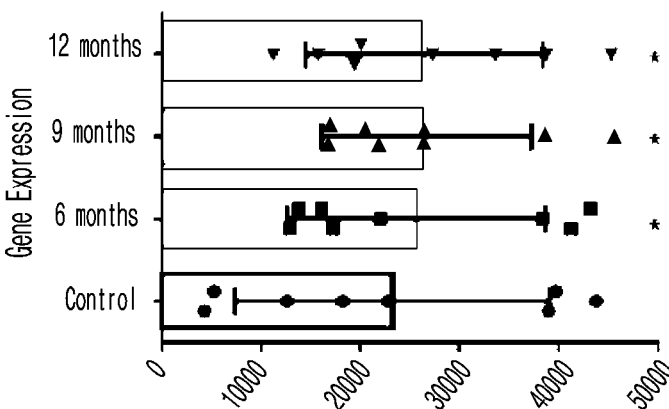
FIG. 4c is a scattered dot plot showing the expression level of the calcium signaling disruption-related gene by month after the onset of Alzheimer's disease.

Particularly, the expressions of the Nmdar, Vdcc, Ryr3, Ip3r, Calm1, Erk/Mapk2 and Bad genes related to calcium signaling by age were shown in FIGS. 4a and 4c by performing RT-PCR as described in Experimental Example <1-1>.

As a result, the expressions of Nmdar, Ryr3, Ip3r and Erk were gradually increased as the disease progressed, and the expressions of Calm1 and Snca were gradually decreased. The expressions of Vdcc and Bad did not change even as the disease progressed (FIG. 4a).

<2-5> Comparison of Mitochondrial Dysfunction-Related Gene Expression

In the brains of Alzheimer's disease patients, mitochondrial function is disrupted because of amyloid beta protein accumulation. Mitochondrial dysfunction leads to reactive oxygen species (ROS) and inflammation, which cause neurodegeneration and cell death. Therefore, the expressions of the genes related to mitochondrial dysfunction by age in mice with Alzheimer's disease were compared.

Figure 5C:
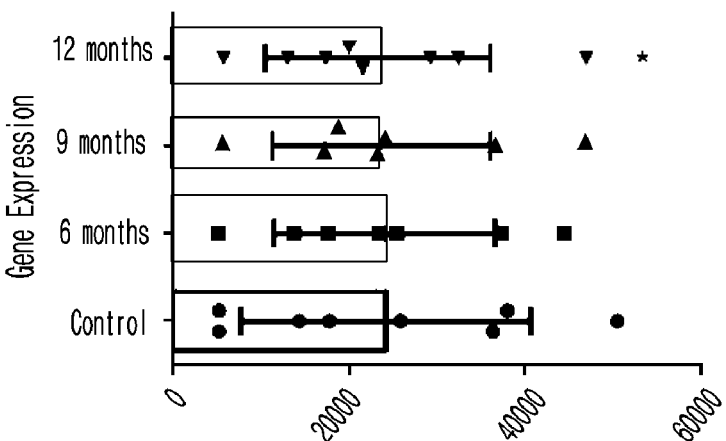
FIG. 5c is a scattered dot plot showing the expression level of the mitochondrial dysfunction-related gene by month after the onset of Alzheimer's disease.

Particularly, the expressions of the Abad, Nmdar, Cx 1-5 and Cycs genes related to mitochondrial dysfunction by age were shown in FIGS. 5a and 5c by performing RT-PCR as described in Experimental Example <1-1>.

As a result, the expressions of Abad and Nmdar were gradually increased as the disease progressed, and the expressions of Cx3, Cx4 and Cx5 were gradually decreased. The expressions of Cx1 and Cx2 did not change even as the disease progressed (FIG. 5a). In addition, it was confirmed that the expressions of the genes related to mitochondrial dysfunction were decreased as Alzheimer's disease progressed (FIG. 5c). Therefore, it was confirmed that the prognosis of Alzheimer's disease can be predicted using the Abad gene whose expression was most significantly changed.

<2-6> Comparison of Inflammation and Apoptosis-Related Gene Expression

Inflammation and apoptosis are the final pathological events in the onset of Alzheimer's disease. Therefore, the expressions of the genes related to inflammation and apoptosis by age in mice with Alzheimer's disease were compared.

Figure 6C:
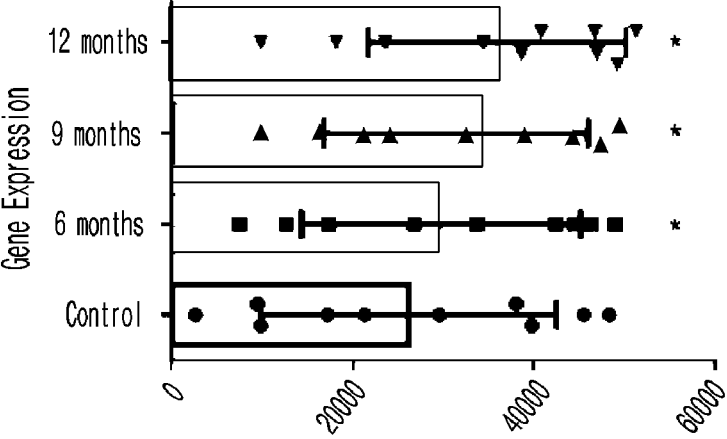
FIG. 6c is a scattered dot plot showing the expression level of the inflammation and apoptosis-related gene by month after the onset of Alzheimer's disease.

Particularly, the expressions of the Tnf, Il1 b, Casp12, Casp3, Casp7, Casp9, Cycs, Nos1 and Bid genes related to inflammation and apoptosis by age were shown in FIGS. 6a and 6c by performing RT-PCR as described in Experimental Example <1-1>.

As a result, the expressions of Tnf, Il1 b, Casp12, Casp3, Casp7, Casp9, Cycs, Nos1 and Bid were gradually increased as the disease progressed (FIG. 6a). In addition, it was confirmed that the expressions of the genes related to inflammation and apoptosis were increased as Alzheimer's disease progressed (FIG. 6c). Therefore, it was confirmed that the prognosis of Alzheimer's disease can be predicted using the Nos1 gene whose expression was most significantly changed.

---

What is claimed is:

1. A composition for predicting a clinical stage of Alzheimer's disease comprising a reagent for measuring a level of mRNA of Serca1 (sarco/endoplasmic reticulum $Ca^{2+}$ ATPase 1) gene, and a cDNA molecule generated from the mRNA, wherein the reagent comprises a primer that specifically binds to the cDNA molecule, and wherein the primer consists of the nucleic acid sequence of SEQ ID NO: 13 or SEQ ID NO: 14.

2. A kit for predicting a clinical stage of Alzheimer's disease comprising the composition of claim 1.

3. The kit according to claim 2, wherein the kit is an RT-PCR (reverse transcription-polymerase chain reaction) kit.

4. A method for predicting a clinical stage of Alzheimer's disease in a subject in need thereof comprising measuring a level of mRNA of Serca1 (sarco/endoplasmic reticulum $Ca^{2+}$ ATPase 1) gene, wherein the measuring of the mRNA level of the Serca1 gene comprises:

i) obtaining a sample from the subject and extracting mRNA from the sample;

ii) performing reverse transcription on the extracted mRNA to generate cDNA;

iii) amplifying the cDNA by performing polymerase chain reaction (PCR) by using a pair of primers consisting of the nucleic acid sequences set forth in SEQ ID NO: 13 and SEQ ID NO: 14; and iv) quantifying the expression level of the mRNA from the amplified cDNA;

wherein:

when the expression level of the mRNA is higher than the expression level of a mRNA of Serca1 isolated from a normal subject, the subject is diagnosed as having early-stage Alzheimer's disease; and when the expression level of the mRNA is lower than the expression level of a mRNA of Serca1 isolated from a normal subject, the subject is diagnosed as having late-stage Alzheimer's disease.

\* \* \* \* \*